US010478313B1

(12) United States Patent
Sweeney, III

(10) Patent No.: US 10,478,313 B1
(45) Date of Patent: Nov. 19, 2019

(54) SPINAL FUSION IMPLANT AND RELATED METHODS

(71) Applicant: NuVasive, Inc., San Diego, CA (US)

(72) Inventor: Thomas M. Sweeney, III, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 608 days.

(21) Appl. No.: 14/594,272

(22) Filed: Jan. 12, 2015

Related U.S. Application Data

(60) Provisional application No. 61/925,874, filed on Jan. 10, 2014, provisional application No. 62/008,781, filed on Jun. 6, 2014.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3008* (2013.01); *A61F 2250/0026* (2013.01)

(58) Field of Classification Search
CPC ...... A61F 2/4455; A61F 2/447; A61F 2/4461; A61F 2/44; A61F 2/442; A61F 2002/3008; A61F 2/4611; A61F 2250/0026
USPC ............................................ 623/17.11–17.16
See application file for complete search history.

(56) References Cited

U.S. PATENT DOCUMENTS

| | | |
|---|---|---|
| 3,848,601 A | 11/1974 | Ma |
| 3,867,728 A | 2/1975 | Stubstad |
| 4,501,269 A | 2/1985 | Bagby |
| 4,657,550 A | 4/1987 | Daher |
| 4,743,256 A | 5/1988 | Brantigan |
| 4,781,591 A | 11/1988 | Allen |
| 4,834,757 A | 5/1989 | Brantigan |
| 4,878,915 A | 11/1989 | Brantigan |
| 4,932,975 A | 6/1990 | Main |
| 4,961,740 A | 10/1990 | Ray |
| 5,015,247 A | 5/1991 | Michelson |
| 5,055,104 A | 10/1991 | Ray |
| 5,071,437 A | 12/1991 | Steffee |
| 5,171,278 A | 12/1992 | Pisharodi |
| 5,192,326 A | 3/1993 | Bao |
| 5,234,460 A | 8/1993 | Stouder |
| 5,263,953 A | 11/1993 | Bagby |
| 5,306,307 A | 4/1994 | Senter |
| 5,312,407 A | 5/1994 | Carter |
| 5,364,400 A | 11/1994 | Rego |
| 5,397,364 A | 3/1995 | Kozak |
| 5,405,391 A | 4/1995 | Hednerson |

(Continued)

FOREIGN PATENT DOCUMENTS

| | | |
|---|---|---|
| AT | 413841 B | 6/2006 |
| AU | 769302 B2 | 5/2002 |

(Continued)

*Primary Examiner* — Zade Coley
*Assistant Examiner* — Jessica Weiss
(74) *Attorney, Agent, or Firm* — NuVasive, Inc.

(57) ABSTRACT

The present invention relates generally to medical devices, systems, and methods for use in surgery. In particular, the disclosed system and methods relate to an intervertebral spinal implant sized and dimensioned for the lumbar spine implantable via a posterior approach. The system includes an implant, instruments for delivering the implant.

17 Claims, 19 Drawing Sheets

(56) References Cited

U.S. PATENT DOCUMENTS

| | | |
|---|---|---|
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen |
| 5,454,811 A | 10/1995 | Huebner |
| 5,458,638 A | 10/1995 | Kuslich |
| 5,489,308 A | 2/1996 | Kuslich |
| 5,492,697 A | 2/1996 | Boyan |
| 5,514,180 A | 5/1996 | Heggeness |
| 5,534,030 A | 7/1996 | Navarro |
| 5,540,688 A | 7/1996 | Navas |
| 5,562,736 A | 10/1996 | Ray |
| 5,571,190 A | 11/1996 | Ulrich |
| 5,571,192 A | 11/1996 | Schonhoffer |
| 5,586,989 A | 12/1996 | Bray |
| 5,593,409 A | 1/1997 | Michelson |
| 5,609,635 A | 3/1997 | Michelson |
| 5,611,800 A | 3/1997 | Davis |
| 5,653,762 A | 8/1997 | Pisharodi |
| 5,658,337 A | 8/1997 | Kohrs |
| 5,665,122 A | 9/1997 | Kambin |
| 5,676,703 A | 10/1997 | Gelbard |
| 5,683,394 A | 11/1997 | Rinner |
| 5,683,464 A | 11/1997 | Wagner |
| 5,700,292 A | 12/1997 | Margulies |
| 5,702,449 A | 12/1997 | McKay |
| 5,702,453 A | 12/1997 | Rabbe |
| 5,702,455 A | 12/1997 | Saggar |
| 5,716,415 A | 2/1998 | Steffee |
| 5,728,159 A | 3/1998 | Stroever |
| 5,755,797 A | 5/1998 | Baumgartner |
| 5,766,252 A | 6/1998 | Henry |
| 5,772,661 A | 6/1998 | Michelson |
| 5,782,832 A | 7/1998 | Larsen |
| 5,785,647 A | 7/1998 | Tompkins |
| 5,785,710 A | 7/1998 | Michelson |
| 5,797,918 A | 8/1998 | McGuire |
| 5,800,550 A | 9/1998 | Sertich |
| 5,836,958 A | 11/1998 | Ralph |
| 5,860,973 A | 1/1999 | Michelson |
| 5,865,845 A | 2/1999 | Thalgott |
| 5,865,848 A | 2/1999 | Baker |
| 5,888,224 A | 3/1999 | Beckers |
| 5,891,147 A | 4/1999 | Moskovitz |
| 5,904,686 A | 5/1999 | Zucherman |
| 5,904,689 A | 5/1999 | Jonjic |
| 5,904,719 A | 5/1999 | Errico |
| 5,910,315 A | 6/1999 | Stevenson |
| 5,928,238 A | 7/1999 | Scarborough |
| 5,947,971 A | 9/1999 | Kuslich |
| 5,968,098 A | 10/1999 | Winslow |
| 5,972,031 A | 10/1999 | Biedermann |
| 6,004,326 A | 12/1999 | Castro |
| 6,008,433 A | 12/1999 | Stone |
| 6,015,436 A | 1/2000 | Schonhoffer |
| 6,033,405 A | 3/2000 | Winslow |
| 6,036,692 A | 3/2000 | Burel |
| 6,039,761 A | 3/2000 | Li |
| 6,042,582 A | 3/2000 | Ray |
| 6,059,829 A | 5/2000 | Schläpfer |
| 6,063,088 A | 5/2000 | Winslow |
| 6,066,174 A | 5/2000 | Farris |
| 6,083,225 A | 7/2000 | Winslow |
| 6,086,613 A | 7/2000 | Camino |
| 6,093,207 A | 7/2000 | Pisharodi |
| 6,096,081 A | 8/2000 | Grivas |
| 6,102,948 A | 8/2000 | Brosnahan |
| 6,136,001 A | 10/2000 | Michelson |
| 6,143,033 A | 11/2000 | Paul |
| 6,159,211 A | 12/2000 | Boriani |
| 6,159,215 A | 12/2000 | Camino |
| 6,165,219 A | 12/2000 | Kohrs |
| 6,193,756 B1 | 2/2001 | Studer |
| D439,338 S | 3/2001 | Huttner |
| 6,206,922 B1 | 3/2001 | Zdeblick |
| 6,210,412 B1 | 4/2001 | Michelson |
| 6,224,607 B1 | 5/2001 | Michelson |
| 6,224,631 B1 | 5/2001 | Kohrs |
| 6,235,059 B1 | 5/2001 | Benezech |
| 6,241,770 B1 | 6/2001 | Michelson |
| 6,241,771 B1 | 6/2001 | Gresser |
| 6,245,072 B1 | 6/2001 | Zdeblick |
| 6,245,108 B1 * | 6/2001 | Biscup .................. A61F 2/4455 606/246 |
| 6,258,125 B1 * | 7/2001 | Paul .......................... A61F 2/28 623/17.11 |
| 6,261,295 B1 | 7/2001 | Nicholson |
| 6,261,296 B1 | 7/2001 | Aebi |
| 6,270,529 B1 | 8/2001 | Terrill-Grisoni |
| 6,277,149 B1 | 8/2001 | Boyle |
| 6,309,403 B1 | 10/2001 | Minor |
| 6,315,795 B1 | 11/2001 | Scarborough |
| 6,319,257 B1 | 11/2001 | Carignan |
| 6,332,883 B1 | 12/2001 | Zucherman |
| 6,350,283 B1 | 2/2002 | Michelson |
| 6,368,325 B1 | 4/2002 | McKinley |
| 6,371,988 B1 | 4/2002 | Pafford |
| 6,371,989 B1 | 4/2002 | Chauvin |
| 6,375,655 B1 | 4/2002 | Zdeblick |
| 6,409,765 B1 | 6/2002 | Bianchi |
| 6,409,766 B1 | 6/2002 | Brett |
| 6,428,541 B1 | 8/2002 | Boyd |
| 6,432,140 B1 | 8/2002 | Lin |
| 6,440,142 B1 | 8/2002 | Ralph |
| 6,447,512 B1 | 9/2002 | Landry |
| 6,447,544 B1 | 9/2002 | Michelson |
| 6,454,806 B1 | 9/2002 | Cohen |
| 6,478,800 B1 | 11/2002 | Fraser |
| 6,482,233 B1 | 11/2002 | Aebi |
| 6,485,517 B1 | 11/2002 | Michelson |
| 6,485,518 B1 | 11/2002 | Cornwall |
| 6,500,206 B1 | 12/2002 | Bryan |
| 6,503,279 B1 | 1/2003 | Webb |
| 6,520,953 B1 | 2/2003 | Schultz |
| 6,524,318 B1 | 2/2003 | Longhini |
| 6,527,773 B1 | 3/2003 | Lin |
| 6,547,823 B2 | 4/2003 | Scarborough |
| 6,557,226 B1 | 5/2003 | Landry |
| 6,558,423 B1 | 5/2003 | Michelson |
| 6,575,899 B1 | 6/2003 | Foley |
| 6,599,294 B2 | 7/2003 | Fuss |
| 6,610,065 B1 | 8/2003 | Branch |
| 6,613,091 B1 | 9/2003 | Zdeblick |
| 6,626,905 B1 | 9/2003 | Schmiel |
| 6,635,086 B2 | 10/2003 | Lin |
| 6,645,206 B1 | 11/2003 | Zdeblick |
| 6,648,895 B2 | 11/2003 | Burkus |
| 6,652,534 B2 | 11/2003 | Zucherman |
| 6,706,067 B2 | 3/2004 | Shimp |
| D488,229 S | 4/2004 | Rinner |
| 6,719,797 B1 | 4/2004 | Ferree |
| 6,723,096 B1 | 4/2004 | Dorchak |
| 6,746,454 B2 | 6/2004 | Winterbottom |
| 6,746,484 B1 | 6/2004 | Liu |
| 6,776,720 B2 | 8/2004 | Bartlett |
| 6,830,570 B1 | 12/2004 | Frey |
| 6,830,574 B2 | 12/2004 | Heckele |
| 6,852,127 B2 | 2/2005 | Varga |
| 6,902,578 B1 | 6/2005 | Anderson |
| 6,926,728 B2 | 8/2005 | Zucherman |
| 6,964,687 B1 | 11/2005 | Bernard |
| 6,979,353 B2 | 12/2005 | Bresina |
| 7,056,341 B2 | 6/2006 | Crozet |
| 7,083,649 B2 | 8/2006 | Zucherman |
| 7,169,183 B2 | 1/2007 | Liu |
| 7,189,234 B2 | 3/2007 | Zucherman |
| 7,204,851 B2 | 4/2007 | Trieu |
| 7,226,483 B2 | 6/2007 | Gerber |
| 7,235,082 B2 | 6/2007 | Bartish |
| 7,252,673 B2 | 8/2007 | Lim |
| 7,255,703 B2 | 8/2007 | Mujwid |
| 7,276,081 B1 | 10/2007 | Coates |
| 7,300,440 B2 | 11/2007 | Zdeblick |

(56) References Cited

U.S. PATENT DOCUMENTS

| | | |
|---|---|---|
| 7,452,359 B1 | 11/2008 | Michelson |
| 7,452,379 B2 | 11/2008 | Mitchell |
| 7,462,195 B1 | 12/2008 | Michelson |
| 7,470,273 B2 | 12/2008 | Dougherty-Shah |
| 7,473,259 B2 | 1/2009 | Jacobs |
| 7,473,268 B2 | 1/2009 | Zucherman |
| 7,473,277 B2 | 1/2009 | Boyer |
| 7,481,839 B2 | 1/2009 | Zucherman |
| 7,503,935 B2 | 3/2009 | Zucherman |
| 7,520,899 B2 | 4/2009 | Zucherman |
| 7,544,208 B1 | 6/2009 | Mueller |
| 7,563,266 B2 | 7/2009 | Camino |
| 7,578,820 B2 | 8/2009 | Moore |
| 7,594,918 B2 | 9/2009 | Brock |
| 7,621,960 B2 | 11/2009 | Boyd |
| 7,637,912 B2 | 12/2009 | Iwasaki |
| 7,662,185 B2 | 2/2010 | Alfaro |
| 7,726,002 B2 | 6/2010 | Shimp |
| 7,749,251 B2 | 7/2010 | Obenchain |
| 7,867,277 B1 * | 1/2011 | Tohmeh ............... A61F 2/4455 623/17.11 |
| 7,887,594 B2 | 2/2011 | Berry |
| 7,901,458 B2 | 3/2011 | Deridder |
| 7,931,656 B2 | 4/2011 | Parry |
| 7,959,634 B2 | 6/2011 | Sennett |
| 7,976,549 B2 | 7/2011 | Dye |
| 7,976,550 B2 | 7/2011 | Trudeau |
| 7,981,156 B2 | 7/2011 | Pafford |
| 7,988,695 B2 | 8/2011 | Dye |
| 7,988,699 B2 | 8/2011 | Martz |
| 8,002,837 B2 | 8/2011 | Stream |
| 8,012,156 B2 | 9/2011 | Marquez Alvarez |
| 8,043,293 B2 | 10/2011 | Warnick |
| 8,048,084 B2 | 11/2011 | Schneid |
| 8,088,163 B1 | 1/2012 | Kleiner |
| 8,097,027 B2 | 1/2012 | Lim |
| 8,105,383 B2 | 1/2012 | Michelson |
| 8,114,092 B2 | 2/2012 | Altarac |
| 8,137,403 B2 | 3/2012 | Michelson |
| 8,152,851 B2 | 4/2012 | Mueller |
| 8,157,845 B2 | 4/2012 | Warnick |
| 8,221,503 B2 | 7/2012 | Garcia |
| 8,246,692 B2 | 8/2012 | Giordano |
| 8,252,060 B2 | 8/2012 | Hansell |
| 8,292,959 B2 | 10/2012 | Webb |
| 8,308,734 B2 | 11/2012 | Evans |
| 8,353,958 B2 | 1/2013 | Edie |
| 8,357,198 B2 | 1/2013 | McGraw |
| 8,372,084 B2 | 2/2013 | Pernsteiner |
| 8,372,148 B2 | 2/2013 | Edie |
| 8,377,137 B2 | 2/2013 | Sournac |
| 8,398,649 B2 | 3/2013 | Koulisis |
| 8,403,991 B2 | 3/2013 | Ullrich |
| 8,409,213 B2 | 4/2013 | Trudeau |
| 8,409,290 B2 | 4/2013 | Zamani |
| 8,414,590 B2 | 4/2013 | Oh |
| 8,425,529 B2 | 4/2013 | Milz |
| 8,444,650 B2 | 5/2013 | Warnick |
| 8,491,653 B2 | 7/2013 | Zucherman |
| 8,506,636 B2 | 8/2013 | Dye |
| 8,512,406 B2 | 8/2013 | White |
| 8,523,874 B2 | 9/2013 | Bonvallet |
| 8,540,725 B2 | 9/2013 | Lim |
| 8,568,452 B2 | 10/2013 | Voorhies |
| 8,568,461 B2 | 10/2013 | Kohm |
| 8,597,357 B2 | 12/2013 | Trudeau |
| 8,603,098 B2 | 12/2013 | Woods |
| 8,603,175 B2 | 12/2013 | Thibodeau |
| 8,652,143 B2 | 2/2014 | McClellan |
| 8,663,331 B2 | 3/2014 | McClellan |
| 8,673,012 B2 | 3/2014 | Smith |
| 8,685,066 B2 | 4/2014 | Stad |
| 8,690,949 B2 | 4/2014 | Messerli |
| 8,696,681 B2 | 4/2014 | Harris |
| 8,734,447 B1 | 5/2014 | Michaelson |
| 8,740,914 B2 | 6/2014 | Crook |
| 8,814,871 B2 | 8/2014 | Mansmann |
| 8,840,621 B2 | 9/2014 | Farr |
| 8,882,841 B2 | 11/2014 | Falahee |
| 8,926,703 B2 | 1/2015 | Michelson |
| 8,956,414 B2 | 2/2015 | Asaad |
| 8,974,464 B2 | 3/2015 | Johnson |
| 8,986,307 B2 | 3/2015 | Kirschman |
| 8,986,389 B2 | 3/2015 | Lim |
| 8,998,924 B2 | 4/2015 | Simpson |
| 9,005,294 B2 | 4/2015 | You |
| 9,011,541 B2 | 4/2015 | Foley |
| 9,028,553 B2 * | 5/2015 | Lindenmann ......... A61F 2/4465 623/17.16 |
| 2002/0165612 A1 * | 11/2002 | Gerber ............... A61B 17/1671 623/17.11 |
| 2003/0036798 A1 | 2/2003 | Alfaro |
| 2003/0105528 A1 * | 6/2003 | Shimp ...................... A61F 2/28 623/17.16 |
| 2003/0199983 A1 * | 10/2003 | Michelson ......... A61B 17/7059 623/17.16 |
| 2004/0098129 A1 | 5/2004 | Lin |
| 2004/0148027 A1 * | 7/2004 | Errico .................. A61F 2/4425 623/17.11 |
| 2004/0176853 A1 | 9/2004 | Sennett |
| 2005/0021145 A1 * | 1/2005 | de Villiers ............ A61F 2/4425 623/17.14 |
| 2005/0096745 A1 * | 5/2005 | Andre .................. A61F 2/4465 623/17.11 |
| 2006/0036258 A1 | 2/2006 | Zucherman |
| 2006/0167461 A1 | 7/2006 | Hawkins |
| 2006/0200166 A1 | 9/2006 | Hanson |
| 2006/0276800 A1 | 12/2006 | Lee |
| 2006/0276801 A1 | 12/2006 | Yerby |
| 2007/0032872 A1 | 2/2007 | Simonton |
| 2007/0043376 A1 | 2/2007 | Leatherbury |
| 2007/0118220 A1 | 5/2007 | Liu |
| 2007/0168040 A1 | 7/2007 | Raymond |
| 2007/0208423 A1 | 9/2007 | Messerli |
| 2007/0270962 A1 | 11/2007 | Arnin |
| 2007/0276365 A1 | 11/2007 | Song |
| 2007/0282441 A1 * | 12/2007 | Stream ................... A61B 17/92 623/17.11 |
| 2007/0293871 A1 | 12/2007 | Ackermann |
| 2008/0065082 A1 | 3/2008 | Chang |
| 2008/0077241 A1 | 3/2008 | Nguyen |
| 2008/0082169 A1 | 4/2008 | Gittings |
| 2008/0103602 A1 | 5/2008 | Berry |
| 2008/0109081 A1 | 5/2008 | Bao |
| 2008/0132902 A1 | 6/2008 | Bertagnoli |
| 2008/0140085 A1 | 6/2008 | Gately |
| 2008/0228276 A1 | 9/2008 | Mathews |
| 2008/0306489 A1 | 12/2008 | Altarac |
| 2008/0306557 A1 | 12/2008 | Altarac |
| 2009/0005874 A1 | 1/2009 | Fleischmann |
| 2009/0182343 A1 | 7/2009 | Trudeau |
| 2010/0131020 A1 | 5/2010 | Heinz |
| 2010/0137922 A1 | 6/2010 | Hunt |
| 2010/0160985 A1 | 6/2010 | Pannu |
| 2010/0204798 A1 * | 8/2010 | Gerbec ................. A61F 2/4465 623/17.16 |
| 2010/0228296 A1 * | 9/2010 | Vraney ................... A61F 2/447 606/279 |
| 2010/0256767 A1 | 10/2010 | Melkent |
| 2011/0071634 A1 | 3/2011 | Jiang |
| 2011/0082555 A1 | 4/2011 | Martz |
| 2011/0106259 A1 * | 5/2011 | Lindenmann ......... A61F 2/4465 623/17.16 |
| 2011/0166654 A1 | 7/2011 | Gately |
| 2011/0238184 A1 | 9/2011 | Zdeblick |
| 2011/0276139 A1 | 11/2011 | Mahoney |
| 2011/0282459 A1 | 11/2011 | McClellan |
| 2012/0029635 A1 | 2/2012 | Schoenhoeffer |
| 2012/0035730 A1 | 2/2012 | Spann |
| 2012/0071980 A1 | 3/2012 | Purcell |
| 2012/0083890 A1 | 4/2012 | McGahan |
| 2012/0158144 A1 * | 6/2012 | Ullrich, Jr. ............ A61F 2/4465 623/17.16 |

(56) References Cited

U.S. PATENT DOCUMENTS

| | | |
|---|---|---|
| 2012/0165943 A1 | 6/2012 | Mangione |
| 2012/0165945 A1 | 6/2012 | Hansell |
| 2012/0185045 A1 | 7/2012 | Morris |
| 2012/0203344 A1 | 8/2012 | Trudeau |
| 2012/0215316 A1 | 8/2012 | Mohr |
| 2012/0277869 A1 | 11/2012 | Siccardi |
| 2012/0283601 A1 | 11/2012 | Daum |
| 2012/0290089 A1* | 11/2012 | Melamed ............ A61F 2/442 623/17.16 |
| 2012/0290091 A1 | 11/2012 | Kirschman |
| 2013/0006362 A1 | 1/2013 | Biedermann |
| 2013/0023937 A1 | 1/2013 | Biedermann |
| 2013/0073046 A1* | 3/2013 | Zaveloff ............. A61F 2/442 623/17.16 |
| 2013/0103102 A1 | 4/2013 | Taylor |
| 2013/0110241 A1 | 5/2013 | Palmatier |
| 2013/0204370 A1 | 8/2013 | Danacioglu |
| 2013/0282018 A1 | 10/2013 | Deridder |
| 2014/0012385 A1 | 1/2014 | Baynham |
| 2014/0039626 A1 | 2/2014 | Mitchell |
| 2014/0039627 A1 | 2/2014 | Weiland |
| 2014/0058512 A1 | 2/2014 | Petersheim |
| 2014/0058518 A1 | 2/2014 | Niemiec |
| 2014/0058522 A1 | 2/2014 | Rhoda |
| 2014/0128929 A1 | 5/2014 | Barrett |
| 2014/0135932 A1 | 5/2014 | Davis |
| 2014/0148907 A1 | 5/2014 | Gately |
| 2014/0172030 A1 | 6/2014 | Harris |
| 2014/0172103 A1 | 6/2014 | O'Neil |
| 2014/0172105 A1 | 6/2014 | Frasier |
| 2014/0172107 A1 | 6/2014 | Thirugnanasambandam |
| 2014/0188228 A1 | 7/2014 | Thibodeau |
| 2014/0316523 A1 | 10/2014 | Errico |
| 2014/0324106 A1* | 10/2014 | Tsuang ............. A61F 2/4465 606/279 |
| 2014/0350682 A1 | 11/2014 | Bagga |
| 2014/0371861 A1 | 12/2014 | Cobb |
| 2014/0371862 A1 | 12/2014 | Milz |
| 2015/0012099 A1 | 1/2015 | Baccelli |
| 2015/0025639 A1 | 1/2015 | Lindenmann |
| 2015/0105860 A1 | 4/2015 | Garner |

FOREIGN PATENT DOCUMENTS

| | | |
|---|---|---|
| AU | 2003266772 B2 | 1/2004 |
| AU | 2004201872 A1 | 5/2004 |
| CN | 201394099 Y | 2/2010 |
| CN | 101732084 A | 6/2010 |
| DE | 2020008011611 U1 | 11/2008 |
| DE | 1020008045174 A1 | 3/2010 |
| EP | 1175878 | 3/2003 |
| EP | 0880938 | 12/2003 |
| EP | 1889587 A2 | 2/2008 |
| EP | 2535021 A1 | 12/2012 |
| EP | 2535022 A1 | 12/2012 |
| KR | 20010023287 A | 3/2001 |
| WO | WO-94004100 | 3/1994 |
| WO | WO-95001810 | 1/1995 |
| WO | WO-9608205 A1 | 3/1996 |
| WO | WO-97033525 | 9/1997 |
| WO | WO-9817208 A1 | 4/1998 |
| WO | WO-01028465 | 4/2001 |
| WO | WO-02017823 | 3/2002 |
| WO | WO-2007054952 | 5/2007 |
| WO | WO-2008021972 | 2/2008 |
| WO | WO-2008049949 | 5/2008 |
| WO | WO-2011056172 | 5/2011 |
| WO | WO-2013007888 | 1/2013 |

* cited by examiner

SPINAL FUSION IMPLANT AND RELATED METHODS

CROSS REFERENCES TO RELATED APPLICATIONS

The present application is a non-provisional patent application claiming the benefit of priority from U.S. Provisional Patent Application Ser. No. 61/925,874, filed on Jan. 10, 2014, entitled "Spinal Implant," and U.S. Provisional Patent Application Ser. No. 62/008,781, filed on Jun. 6, 2014, entitled "Spinal Implant," the entire contents of which are hereby expressly incorporated by reference into this disclosure as if set forth in their entirety herein.

FIELD

The present invention relates generally to spinal surgery and, more particularly, to a device for spinal fusion comprising a spinal fusion implant of non-bone construction to be introduced into any variety of spinal target sites.

BACKGROUND

Currently there nearly 500,000 spine fusion procedures performed each year in the United States. One of the causes of back pain and disability derives from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Transforaminal lumbar interbody fusion (TLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient and involves placing a fusion device into the intervertebral disc space. Introducing the intervertebral implant serves to restore the height ("disc height") between adjacent vertebrae, which reduces if not eliminates neural impingement commonly associated with a damaged or diseased disc.

SUMMARY OF THE INVENTION

The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant may further include a surface coating to encourage bone growth onto endplate contacting surfaces. The spinal fusion implant of the present invention may be provided in any number of suitable shapes and sizes depending upon the particular surgical procedure or need. The spinal fusion implant may be dimensioned for use in any part of the spine (e.g. cervical, lumbar and/or thoracic) without departing from the scope of the present invention. The implant may be dimensioned, by way of example only, having a width ranging between 8 and 16 mm, a height ranging between 8 and 18 mm, and a length ranging between 28 and 40 mm.

According to one broad aspect of the present invention, the spinal fusion implant includes top and bottom sides, first and second lateral ends, and anterior and posterior sides. The spinal fusion implant of the present invention may be used to provide temporary or permanent fixation along an orthopedic target site. To do so, the spinal fusion implant may be introduced into a disc space while locked to a surgical insertion instrument and thereafter manipulated in the desired orientation and released. Once deposited in the intervertebral disc space between adjacent vertebrae (V1 and V2), the spinal fusion implant of the present invention effects fusion over time as the natural healing process integrates and binds the implant.

The spinal fusion implant of the present invention may be provided with any number of additional features for promoting fusion, such as one or more apertures extending between the top and bottom sides which allow a boney bridge to form through the spinal fusion implant. The spinal implant may also be preferably equipped with one or more lateral openings which facilitate visualization at the time of implantation and at subsequent clinical evaluations.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom sides of the implant.

According to a further aspect of the present invention, the spinal fusion implant may be provided with one or more radiographic markers disposed within any one of the first and second lateral ends and anterior and posterior sides. These markers allow for a more detailed visualization of the implant during and after insertion (through radiography) and allow for a more accurate and effective placement of the implant.

According to a still further aspect of the present invention, the first lateral end (leading end) of the spinal fusion implant has a conical (bullet-shaped) shape including a pair of first tapered (angled) surfaces and a pair of second tapered (angled) surfaces which function to distract the vertebrae adjacent to the target intervertebral space during insertion of the spinal fusion implant. Furthermore, the anterior side of the spinal fusion implant is shaped to match the curvature of the posterior aspect of the annulus fibrosus at the anterior aspect of the intervertebral space.

According to a still further aspect of the present invention, the spinal fusion implant may be introduced into a spinal target site through use of any of a variety of suitable insertion instruments having the capability to engage the implant and position it within the intervertebral space. The spinal fusion implant is capable of being used in minimally invasive surgical procedures, needing only a relatively small operative corridor for insertion.

According to a still further aspect of the present invention, the spinal fusion implant and/or insertion instrument may be provided with one or more markings to aid in verifying desired positioning of the spinal fusion implant during and after its placement into the intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 15 C is a plan view of the distal end of the insertion instrument of FIG. 12 in the unlocked configuration;

FIG. 17 B is a plan view of the distal end of the insertion instrument of FIG. 12 in the first transitional position of FIG. 17 A;

FIG. 18 B is a plan view of the distal end of the insertion instrument of FIG. 12 in the second transitional position of FIG. 18 A;

FIG. 19 C is a plan view of the distal end of the insertion instrument of FIG. 12 in the locked configuration;

FIG. 20 C is a plan view of the distal end of the insertion instrument of FIG. 12 in the pivot configuration;

FIG. 23 B is a user's view of the spinal fusion implant in the first alignment position;

FIG. 23 C is a view of the spinal fusion implant of FIG. 1 in a second alignment position as indicated by external alignment markers;

FIG. 23 D is a user's view of the spinal fusion implant in the second alignment position;

FIG. 23 E is a view of the spinal fusion implant of FIG. 1 in a third alignment position as indicated by external alignment markers;

FIG. 23 F is a user's view of the spinal fusion implant in the third alignment position;

FIG. 23 G is a view of the spinal fusion implant of FIG. 1 in a fourth alignment position as indicated by external alignment markers;

FIG. 23 H is a user's view of the spinal fusion implant in the fourth alignment position;

FIG. 24 B is a perspective view of the spinal fusion implant coupled to the insertion instrument in a second alignment position as indicated by external alignment markers on the implant and instrument;

DESCRIPTION OF THE PREFERRED EMBODIMENT

Figure 1:
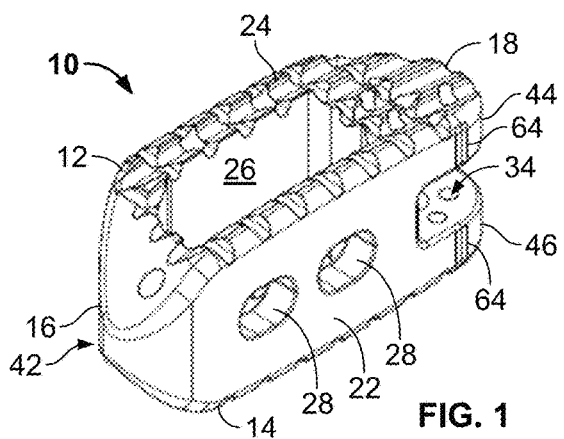
FIG. 1 is a perspective view of an example of a spinal fusion implant according to a first embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant, system, and methods disclosed herein boast a variety of inventive features and components that warrant patent protection, both individually and in combination.

FIGS. 1-9 illustrate a spinal fusion implant 10 according to a first broad aspect of the present invention. The spinal fusion implant 10 may be constructed of any suitable non-bone composition, including but not limited to polymer compositions (e. g. poly-ether-ether-ketone (PEEK) and/or poly-ether-ketone-ketone (PEKK)), ceramic, metal (e.g. titanium) and/or any combination of polymer compositions, ceramic and metal. The spinal fusion implant 10 may further include a surface coating to encourage bone growth onto endplate contacting surfaces (e.g. titanium spray coating). The spinal fusion implant 10 includes a top side 12, a bottom side 14, a first lateral end 16, a second lateral end 18, an anterior side 20, and a posterior side 22 (each defined relative to the regions of the target disc space when implanted into the final position). According to a preferred method of implantation, the spinal fusion implant 10 may be implanted into the anterior portion of the disc space from a posterior approach such that first lateral end 16 is the leading end and second lateral end 18 is the trailing end during insertion.

The spinal fusion implant 10 of the present invention may be provided in any number of shapes and sizes depending upon the particular surgical procedure or need. By way of example only, the spinal fusion implant 10 may have a width ranging between 8 and 16 mm (width being distance between anterior and posterior sides 20, 22), a height ranging between 8 and 18 mm (height being distance between top and bottom sides 12, 14), and a length ranging between 28 and 40 mm (length being distance between first and second lateral ends 16, 18).

The spinal fusion implant 10 of the present invention may be used to provide temporary or permanent fixation within an orthopedic target site. To do so, the spinal fusion implant 10 may be introduced into a disc space while locked to a surgical insertion instrument and thereafter employed in the desired orientation and released, as explained in further detail below. Once deposited in the disc space, the spinal fusion implant 10 of the present invention effects spinal fusion over time as the natural healing process integrates and binds the implant.

Figure 3:
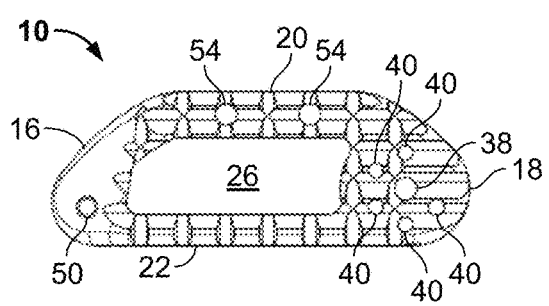
FIG. 3 is a plan view of the top side of the spinal fusion implant of FIG. 1.
Figure 4:
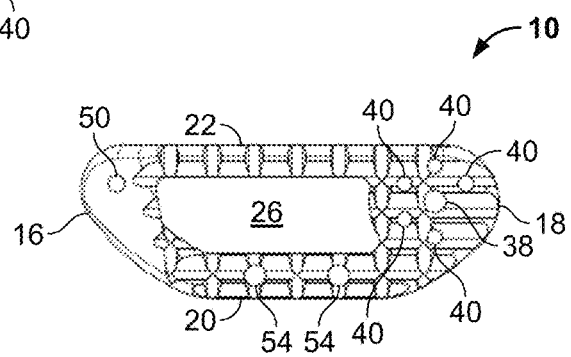
FIG. 4 is a plan view of the bottom side of the spinal fusion implant of FIG. 1.
Figure 5:
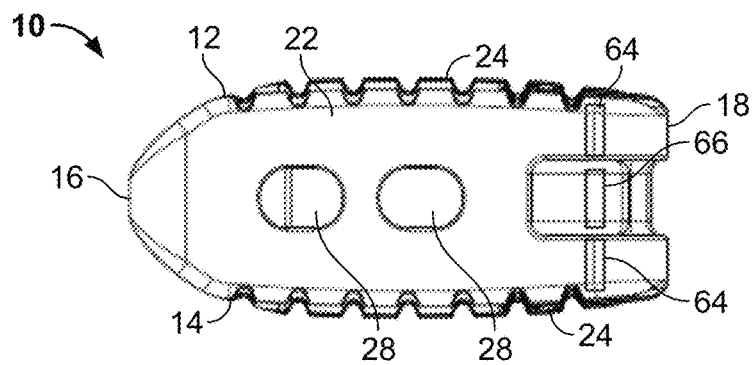
FIG. 5 is a plan view of the posterior side of the spinal fusion implant of FIG. 1.
Figure 6:
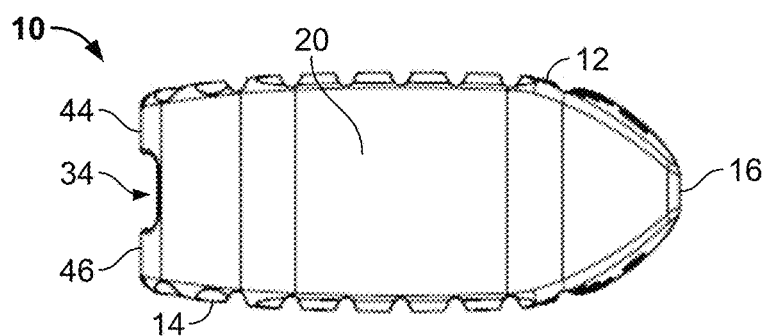
FIG. 6 is a plan view of the anterior side of the spinal fusion implant of FIG. 1.

FIGS. 3-4 illustrate the top and bottom sides 12, 14, respectively, of the spinal fusion implant 10. The top and bottom sides 12, 14 are configured to engage the vertebral bodies adjoining the target disc space. Accordingly, the top and bottom sides 12, 14 each preferably include a plurality of anti-migration features designed to increase the friction between the spinal fusion implant 10 and the adjacent contacting surfaces of the vertebral bodies. Such anti-migration features may include ridges (or teeth) 24 provided along the top side 12 and/or bottom side 14. The friction prohibits migration of the implant 10 after insertion into the intervertebral space and during the propagation of natural bony fusion.

It can be appreciated by one skilled in the art that the top and bottom side 12, 14 may be configured in any number of suitable shapes to better match the natural contours of the vertebral end plates. For example, top and bottom sides 12, 14 may be generally planar, generally concave, generally convex, or a combination of concave and convex (a generally convex implant is shown, for example in the embodiment of FIGS. 1-9). Top and bottom sides 12, 14, for example, may each be at least one of generally planar, generally convex, and generally concave. According to an additional embodiment (not shown), the top and bottom sides 12, 14 may be angled between the anterior side 18 and the posterior side 20. In lumbar applications, distance between top and bottom sides 12, 14 at the posterior side 20 will preferably be shorter in height than at the anterior side 18 such that the implant 10 tapers down from anterior side 20 to posterior side 22. For example, the posterior-to-anterior angle of the tapered top and bottom sides 12, 14 may range from 5 and 15 degrees relative to a horizontal axis. In this manner, the spinal fusion implant 10 helps maintain the adjacent vertebral bodies in lordosis, which is the natural curvature found in the lumbar region of the spine.

The spinal fusion implant 10 includes a large aperture 26 extending between top and bottom sides 12, 14. FIGS. 1-4 illustrate aperture 26 extending in a vertical fashion between the top and bottom sides 12, 14. The aperture 26 may be provided in any number of suitable shapes, including but not limited to generally circular, generally oblong, generally triangular and/or generally rectangular. This single large aperture 26 is an additional feature for promoting fusion between the upper and lower vertebral bodies which allow a boney bridge to form through the spinal fusion implant 10.

According to another further aspect of the present invention, this fusion may be facilitated or augmented by including osteoinductive material(s) within the aperture 26 and/or adjacent to the spinal fusion implant 10. Such osteoinductive materials may be introduced before, during, or after insertion of the spinal fusion implant 10 of the present invention, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D, L-lactide-co-glycolide) based polymers.

According to some embodiments, the implant may be shaped to match the anatomical constraints of the intervertebral space. By way of example, the width of the spinal fusion implant 10 may shorter at the anterior side 20 than at the posterior side 22 and the implant 10 may be curved along the anterior side 20 to match the curvature of the annulus fibrosus of the intervertebral disc (shown by way of example in FIG. 3-4).

Figure 11:
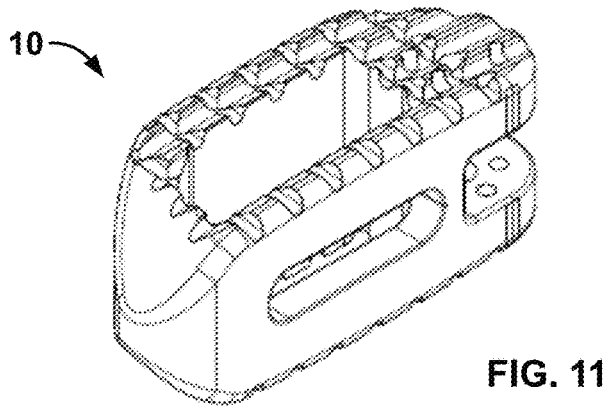
FIG. 11 is a perspective view of an example of a spinal fusion implant according to an alternate embodiment of the present invention.
Figure 12:
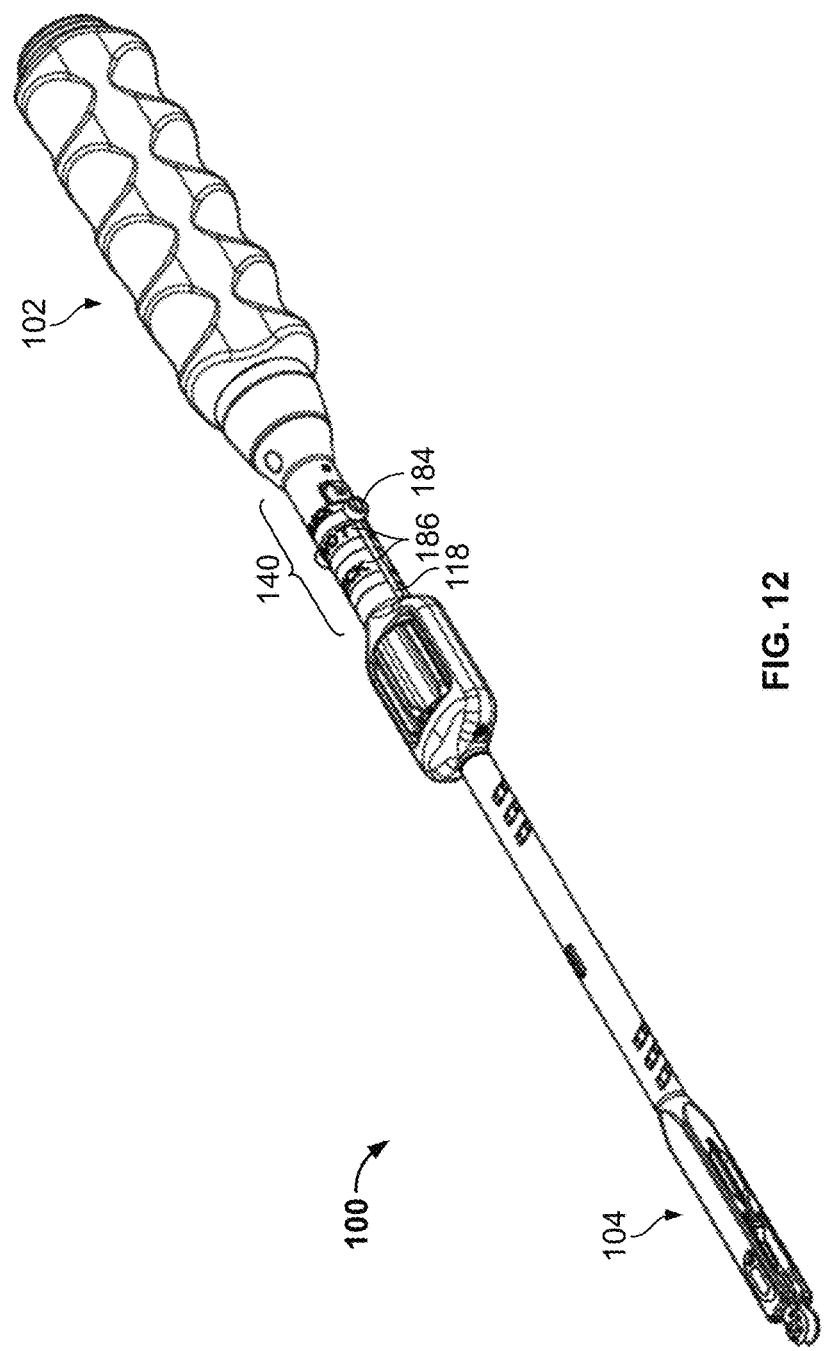
FIG. 12 is a perspective view of an example insertion instrument according to one embodiment of the present invention.

The spinal fusion implant 10 may be further provided with one or more posterior apertures 28 extending generally perpendicularly therethrough from the posterior side 22 to aperture 26. Posterior apertures 28 function to provide visualization at the time of implantation and at subsequent clinical evaluations. Posterior apertures 28 may be provided in any of a variety of suitable shapes, including but not limited to generally circular, generally oblong, generally triangular, generally rectangular, and/or generally oval (shown by example in FIG. 5), or any combination thereof. Although the spinal fusion implant 10 examples shown in FIGS. 1 and 11 each include a pair of posterior apertures 28, the spinal fusion implant 10 may include any number of posterior apertures 28 as desired (e.g. one posterior aperture 28 as shown in the embodiment of FIG. 12).

More specifically, based on the generally radiolucent nature of the implant 10, the lateral apertures 28 provide the ability to visualize the interior of the implant 10 during X-ray and/or other suitable imaging techniques which are undertaken from the lateral perspective of the implant 10. If fusion has taken place, the lateral apertures 28 will provide a method for the surgeon to make follow up assessments as to the degree of fusion without any visual interference from the spinal fusion implant 10. Further, the lateral apertures 28 will provide an avenue for cellular migration to the exterior of the spinal fusion implant 10. Thus the spinal fusion implant 10 will serve as additional scaffolding for bone fusion on the exterior of the spinal fusion implant 10.

Figure 7:
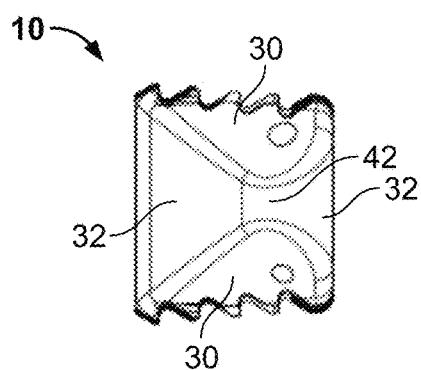
FIG. 7 is a plan view of a first lateral end of the spinal fusion implant of FIG. 1.

FIG. 7 illustrates the first lateral end (or insertion end) 16 of the spinal fusion implant 10. The first lateral end 16, as best illustrated in FIGS. 1 and 7 has a conical (bullet-shaped) tip 42 including a pair of first tapered (angled) surfaces 32 and a pair of second tapered (angled) surfaces 30. First tapered surfaces 32 extend between anterior side 20 and posterior side 22 and the first lateral end 16 and second tapered surfaces 30 extend between top and bottom sides 12, 14 and the first lateral end 16. The conical tip 42 aids in ease of insertion and functions to distract the vertebrae adjacent to the target intervertebral space during insertion of the spinal fusion implant 10.

Figure 2:
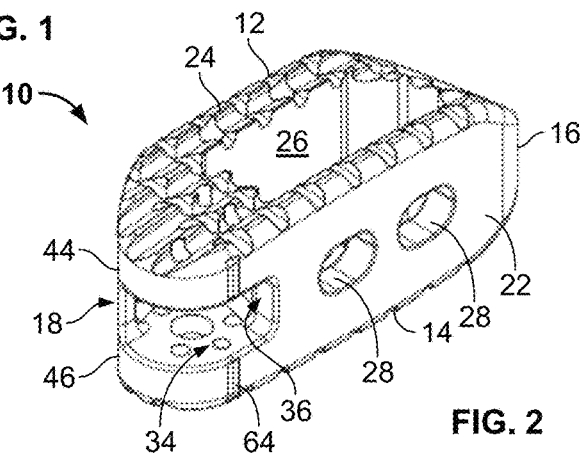
FIG. 2 is a second perspective view of the spinal fusion implant of FIG. 1.
Figure 8:
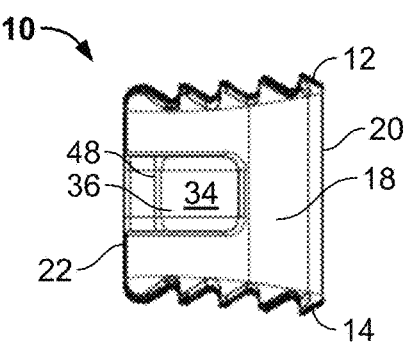
FIG. 8 is a plan view of a second lateral end of the spinal fusion implant of FIG. 1.

FIGS. 2 and 8 illustrate the second lateral end (trailing end) 18 of the spinal fusion implant 10. The second lateral end 18 includes a top portion 44 and a bottom portion 46 defining the upper and lower bounds of an engagement recess 34. Engagement recess 34 sized and dimensioned to receive an insertion tool 100. According to some embodiments, the engagement recess 34 includes a pivot groove 36, a pivot stop 48, large central protrusion aperture 38, and one or more small radial protrusion apertures 40.

The spinal fusion implant 10 of the present invention may also be provided with one or more radiographic markers to allow for visual determination of desired implant position and alignment. The radiographic markers may be provided in any size or shape suitable to facilitate effective and accurate visualization of implant placement. The radiographic markers may be manufactured from any of a variety of suitable radiopaque materials, including but not limited to a metal, ceramic, and/or polymer material, preferably having radiopaque characteristics.

According to one or more embodiments, the spinal fusion implant 10 includes at least one radiographic marker. The one or more radiographic markers each comprise a unitary element (e.g., a cylinder such as an elongated cylinder) extending through the top side 12 and the bottom side 14. Alternatively, each radiographic marker may comprise a shorter element which only extends through a single side. Alternatively, each radiographic marker may comprise a shorter element that does not extend beyond either side.

The spinal fusion implant 10 may possess radiographic markers in the form of elongated cylinders extending generally perpendicularly through the implant 10 between the top and bottom sides 12, 14. As best appreciated in FIGS. 3, 4, and 9, according to a first embodiment, the spinal fusion implant 10 may be provided with a first radiographic marker 50 positioned at or near the conical tip 42 of the first lateral end 16. Preferably, the first radiographic marker 50 is positioned at least partially between first tapered surfaces 30. The second lateral end 18 (of spinal fusion implant 10 may be provided with second and third radiographic markers 52, one positioned at least partially within the top portion 44 and one positioned at least partially within bottom portion 46. Further, the anterior side 20 may contain fourth and fifth radiographic markers 54, each of which being at least partially positioned within the wall of anterior side 20 between top and bottom sides 12, 14. As will be discussed in further detail below, the radiographic markers 50, 52, 54 may be examined during placement and after final placement of the spinal fusion implant 10 for desired position and alignment of the implant within the intervertebral disc space.

Figure 10:
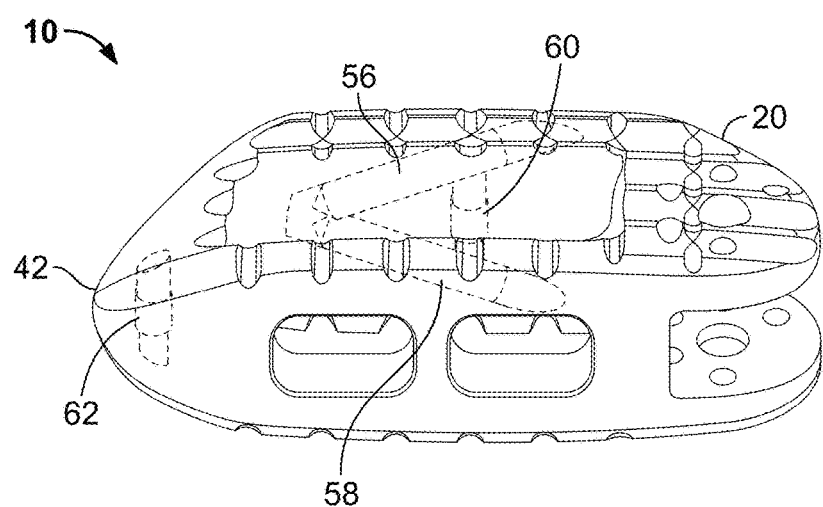
FIG. 10 is a plan view of the spinal fusion implant of FIG. 1 showing internal radiographic markers according to a second embodiment.

According to a second embodiment shown by way of example in FIG. 10, the spinal implant 10 may be provided with a first radiographic marker 56 extending from the top side 12 to at least partially within the wall of anterior side 20 and a second radiographic marker 58 extending from the bottom side 14 to at least partially within the wall of anterior side 20 of the spinal fusion implant 10. Preferably, markers 56, 58 converge to form a directional angle. The anterior side 20 may further contain a third radiographic marker 60 preferably positioned entirely within the implant and located at the midline between first and second lateral ends 16, 18. First lateral end 16 may contain a fourth radiographic marker 62 at conical tip 42. As will be discussed in further detail below, radiographic markers 56, 58, 60, 62 may be examined during placement and after final placement of the spinal fusion implant for desired position and alignment of the implant within the intervertebral disc space.

It is to be appreciated that while the embodiments shown in FIGS. 1-10 include radiographic markers, the incorporation of such radiographic markers is optional. By way of example, the embodiment shown in FIG. 11 does not include such radiographic markers.

The spinal fusion implant 10 may optionally include strategically placed visual markings its outer surfaces to help identify rotational orientation during the insertion process. By way of example, the visual markings may comprise a plurality of vertical stripes 64, 66 that indicate desired positioning when they are in alignment. By way of example, they may appear as a single, unbroken line to the user. Until the spinal fusion implant 10 is positioned correctly, the vertical stripes 64, 66 will appear as separate stripes. As shown by example in FIG. 5, the spinal fusion implant 10 may have a pair of vertical stripes 64 positioned on the second lateral end 18 adjacent the engagement recess 34 in alignment with one another. The spinal fusion implant 10 may have another vertical stripe 66 located on the inside of engagement recess 34. By spacing the markings apart from one another as shown, as the spinal implant 10 rotates into position, the vertical stripes 64, 66 move in relation to one another from the viewing perspective as will be discussed below with respect to FIGS. 23 A-H. The relative movement or position allows the user to identify the current rotational orientation of the spinal fusion implant 10. The markings can further be aligned such that they create a specific orientation when the spinal fusion implant 10 is in a desired position (e.g. the vertical stripes 64, 66 can align and create a straight line when in the desired final position). By way of example, the vertical stripes 64, 66 may comprise laser etching on the spinal fusion implant 10 or a strip of visually contrasting material attached to, or embedded within, the implant, however other visual indicators are possible as well.

The spinal fusion implant 10 may be introduced into a spinal target site through use of any of a variety of suitable surgical instruments having the capability to engage the implant 10. As described in FIGS. 12-24, the present invention includes a plurality of inserters which provide the user with a suite of choices for implanting the spinal fusion implant 10. According to a broad aspect, the insertion instruments include a proximal region 102, a distal region 104, an elongate tubular element 106, and an inner shaft 108.

Figure 13:
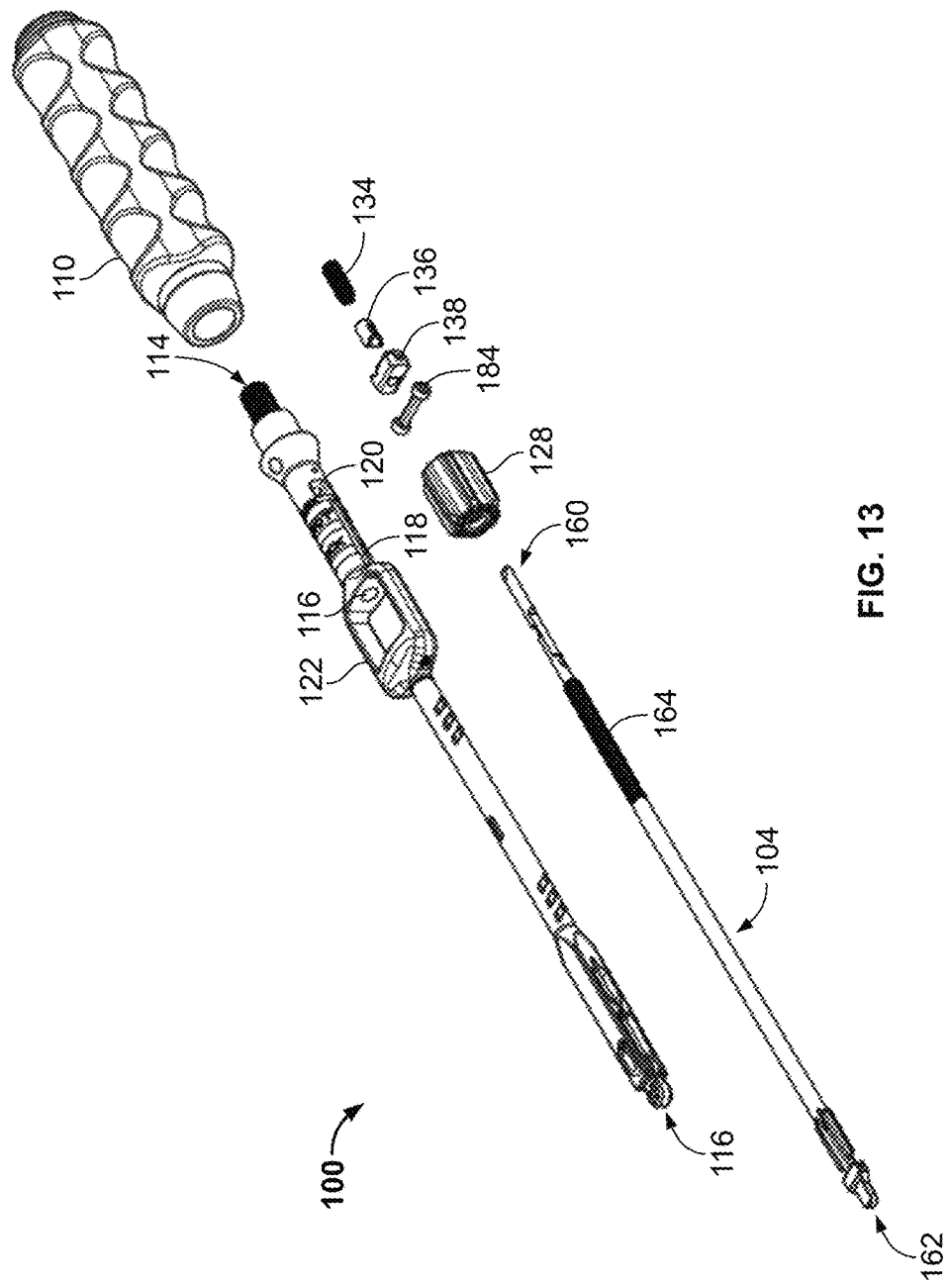
FIG. 13 is an exploded perspective view of the insertion instrument of FIG. 12.

As depicted in FIGS. 12-13, the handle 110 is generally disposed at the proximal region 102 of the insertion instrument 100. The elongate tubular element 106 is comprised of a proximal end 112, a distal end 114, and an inner bore 116 extending between proximal and distal ends 112, 114. At or near the proximal end 112 are positioned bilateral longitudinal slots 118 and bilateral button slots 120 and a thumbwheel housing 122. At or near the distal end 114 are a pair of flexible arms and a pair of distal insertion members 126.

Figure 22:
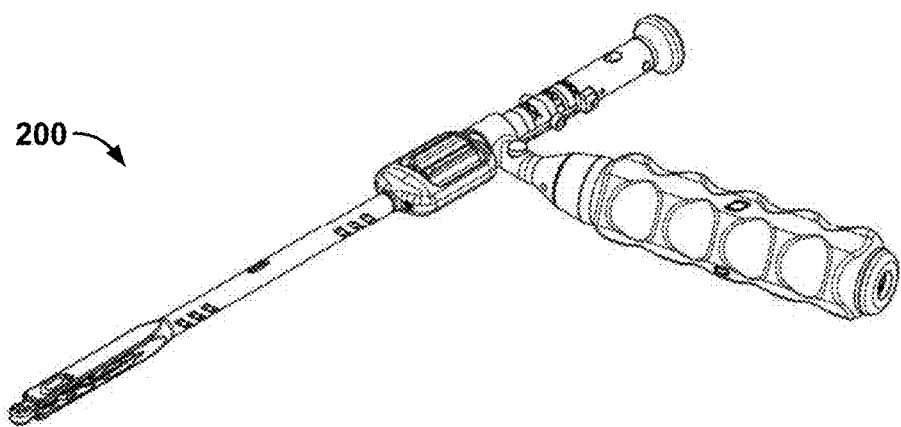
FIG. 22 is a perspective view of an example insertion instrument according to a second embodiment of the present invention.
Figure 23B:
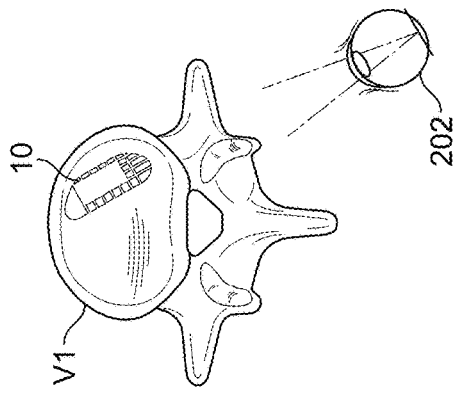
FIG. 23 A is a view of the spinal fusion implant of FIG. 1 in a first alignment position as indicated by external alignment markers.
Figure 23D:
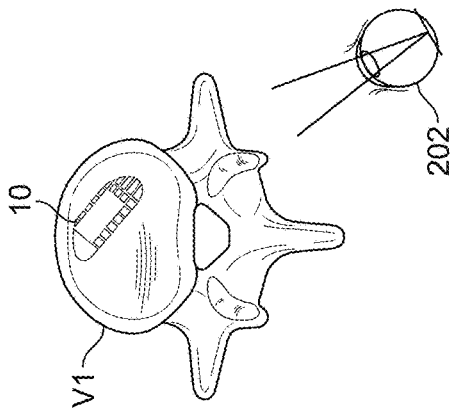
Figure 23A:
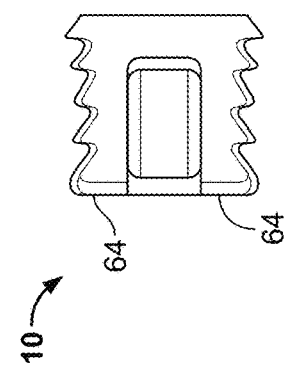
Figure 23C:
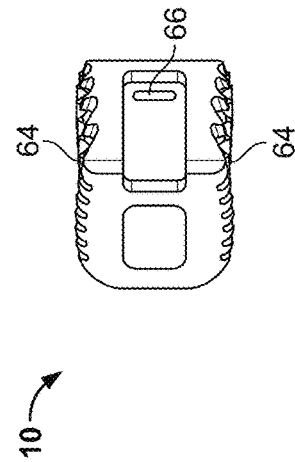
Figure 23F:
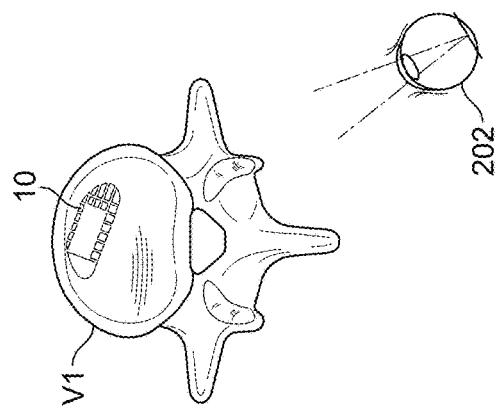
Figure 23H:
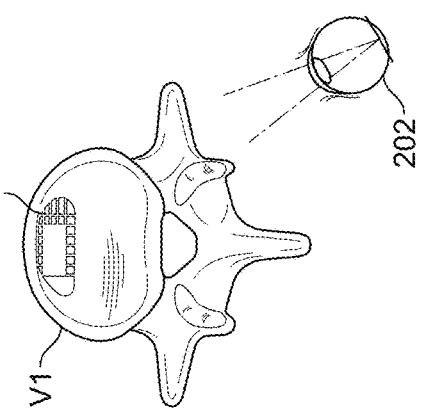
Figure 23E:
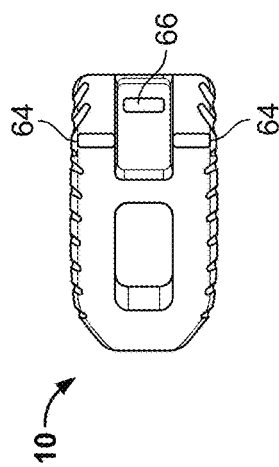
Figure 23G:
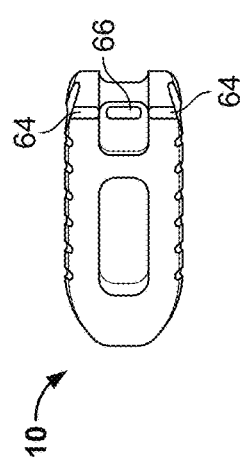

The handle 110 is in a fixed relationship with the elongate tubular element 106. The handle 110 may be aligned with the elongate tubular element 106 (as shown in FIG. 12), but may also be positioned offset from the elongate tubular element 106 (as shown in FIG. 22). The handle 110 is also in a fixed relationship with the thumbwheel housing 122 allowing easy handling by the user. By way of example, the thumbwheel housing 122 holds a thumbwheel 128, a set screw 130, and at least one spacer 132. Because the handle 110 is fixed, the user has easy access to the thumbwheel 128 and can easily and stably turn the thumbwheel 128 relative to the thumbwheel housing 122. The threaded portion 164 of the inner shaft 108 is threadably received by the inner threaded portion of the thumbwheel 128 and is freely rotatable within the thumbwheel housing 122. The user may then employ the thumbwheel 128 to rotate the inner shaft 108 thereby advancing and retracting the distal insertion head 168 of the inner shaft 108 within the elongate tubular element 106 to lock the spinal fusion implant 10 to the insertion instrument 100 and position it within the intervertebral space as will be described in greater detail below.

The elongate tubular element 106 is generally cylindrical and of a length sufficient to allow the device to span from the surgical target site to a location sufficiently outside the patient's body so the handle 110 and the thumbwheel housing 122 can be easily accessed by the user. The elongate tubular element 106 is dimensioned to receive a spring 134, a cam 136, a lock button 138, a proximal gauge 140, and the inner shaft 108 into the inner bore 116.

Figure 14:
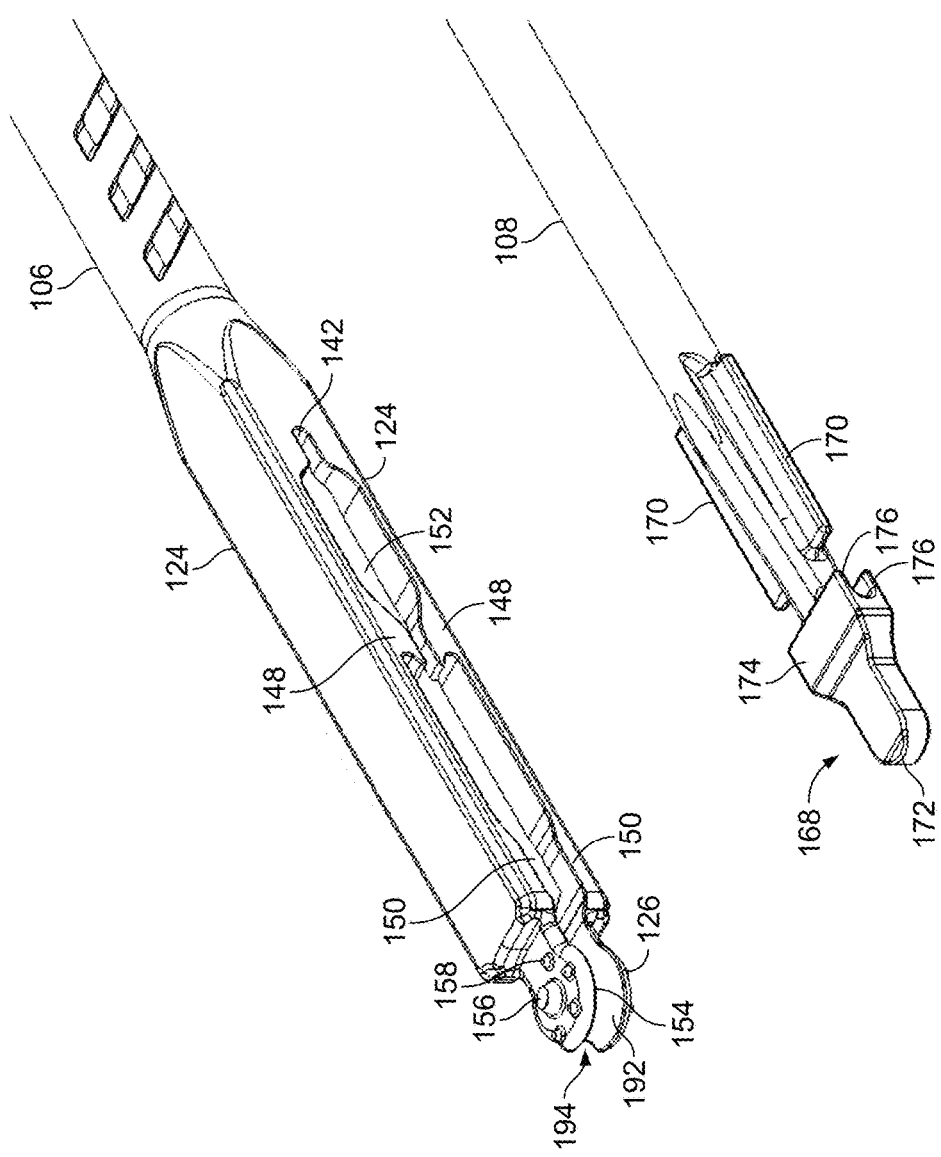
FIG. 14 is a detailed exploded perspective view of the distal end of the insertion instrument of FIG. 12.

Referring now to FIG. 14, the flexible arms 124 bifurcate at medial grooves 142 on opposing sides of the insertion instrument 100. Preferably, there are two flexible arms 124, each comprising a distal end, an interior surface, a proximal advancement ramp 148, and a distal advancement ramp 150. Extending distally from medial grooves, the space between the interior surfaces 148 of the flexible arms 124 form a lateral wing-receiving channel 152.

The distal end 144 of each flexible arm 124 terminates in a distal insertion member 126. The distal insertion members 126 are shaped to engage the engagement recess 34 of the spinal fusion implant 10. As best seen in FIG. 14, each distal insertion member includes a rounded distal protrusion 154, a large protrusions 156, and a plurality of small protrusions 158. While the embodiment shown here includes one large central protrusion 156 and four small radial protrusion 158, it is to be appreciated that any combination of shapes, and numbers of shapes are contemplated to mate with the spinal fusion implant 10. Rounded distal protrusion 154 terminates at flat face 194. Rounded distal protrusion 154 is sized and dimensioned to be generally complementary in shape to the groove in the engagement recess such that it may freely pivot within the recess until such location that flat face 194 contacts a pivot stop 48 within the pivot groove 36 of the engagement recess 34. The radial position of flat face 194 along the outer surface of rounded distal protrusion 154 and the position of pivot stop 48 within the pivot groove 36 determines the degree to which the insertion instrument 100 is able to pivot within the engagement recess 34. The embodiment shown in FIGS. 12-21, the insertion instrument 100 is capable of pivoting the spinal fusion implant 90 degrees and the embodiment shown in FIG. 22, the insertion instrument 100 is capable of pivoting 60 degrees, however any pivot angle is possible and contemplated herein.

Large central protrusion 154 and small radial protrusions 156 extend outwardly from the distal insertion members 126. Large central protrusion member 156 has a height that is larger than the heights of each of the small radial protrusions 158. Large central protrusion 154 is sized and dimensioned to engage with the large central protrusion aperture 38 when the insertion instrument 100 is in the lock and pivot configurations but not the unlock configuration. Small radial protrusions 158 are sized and dimensioned to engage with the small radial protrusion apertures 40 when the insertion instrument 100 is in the lock configuration but not when it is in the unlock or pivot configurations. As will be described in greater detail below, in the pivot configuration, the spinal fusion implant 10 pivots into position within the intervertebral disc space about large central protrusion member 156.

The inner shaft 108 is sized and dimensioned to be disposed within the inner bore 116 of the elongate tubular element 106. The inner shaft 108 is comprised of a proximal end 160, a distal end 162, and a threaded intermediate portion 164. The threaded portion 164 engages the thumbwheel 128 to advance and retract the inner shaft 108 within the elongate tubular element 106. The proximal end 160 includes a cutout portion 166 which comprise parts of the actuation assembly 178 and serves to permit and/or limit translation of the inner shaft 108 depending on the configuration of the insertion instrument 100 (e.g. a locked, pivot, or unlocked configuration) as discussed below. The distal end 162 comprises a distal insertion head 168 and lateral wings 170. Distal insertion head 168 is further comprised of an advancement head 172, a support spacer 174, and upper and lower abutment prongs 176.

Preferably, the insertion instrument 100 is operable to switch between multiple configurations. According to some embodiment, the location of the inner shaft 108 within the elongate tubular element 106 dictates the configuration that the insertion instrument 100. Such configurations include, but are not limited to locked, pivot, and unlocked configurations. Components of, and components housed within, the elongate tubular element 106 and cooperate with the inner shaft 108 in an actuation assembly 178 to switch between configurations. Shown by way of example in FIGS. 15 A-B, 17 A, 18 A, 19 A-B, and 20 A-B, actuation assembly 178, includes spring 134, cam 136, button 138, proximal gauge 140, and cutout 166. According to the embodiment shown, button 138 is seated within the elongate tubular element 106 at the button slots 120 and positioned around the inner shaft region 180 as will be described below. Button 138 also contains a notch 182 that prevents the inner shaft 108 from translating in the locked position when the inner shaft 108 and button 138 are in locked alignment. Cam 136 and spring 134 are also seated within the elongate tubular element 106 and positioned around the inner shaft 106. As will be described below, advancement of the thumbwheel 128 causes spring 134 to impart a force on the cam 136 which causes button 138 to move between the locked and unlocked positions. The proximal gauge 140 is comprised of a pin 184 that extends through the elongate tubular element 106 and travels along the bilateral longitudinal slots 118 as the inner shaft 108 translates through the elongate tubular element 106. Position indicators 186 on the exterior of the elongate tubular element 106 provide visual feedback to the user of the configuration the insertion instrument 100.

According to some embodiments, insertion instruments may optionally include visualization markers on the distal end 104 to provide an indication of the orientation of the spinal fusion implant 10. As will be described below with respect to FIGS. 24 A-B, insertion instrument 100 may include a stripe 196 which may be, for example laser etching or a strip of visually contrasting material at or near the distal end 104. The stripe 196 may interact with vertical stripes 66 on the spinal fusion implant 10 to provide an indication of the rotational orientation of the spinal fusion implant in relation to the position of the insertion instrument as will be described in greater detail below.

Figure 15A:
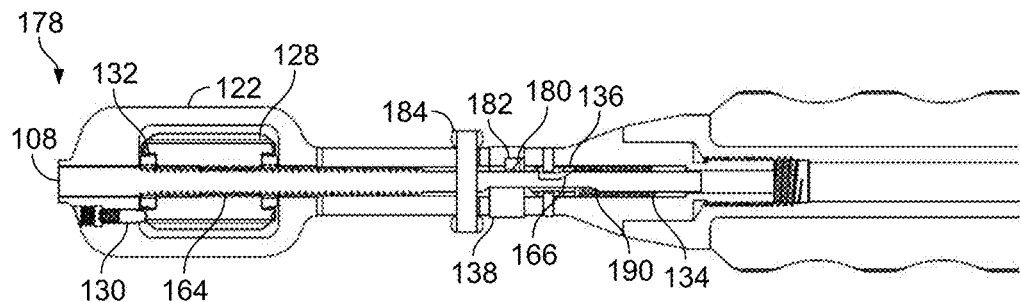
FIGS. 15 A-B are cross sectional views of the proximal end of the insertion instrument of FIG. 12 in an unlocked configuration.
Figure 15B:
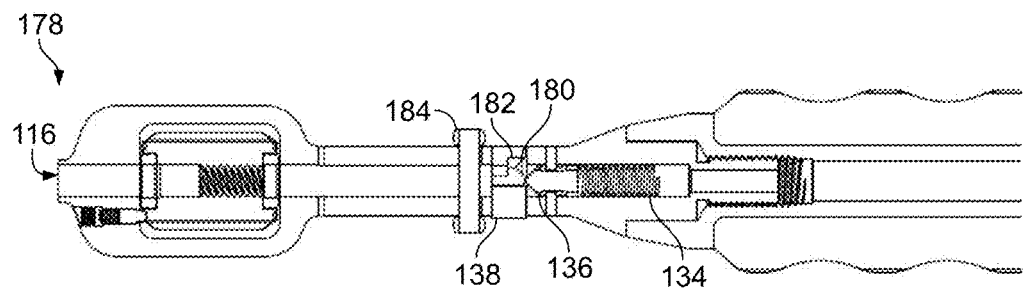
Figure 15C:
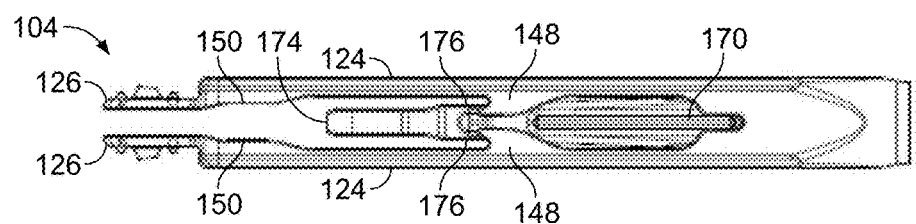
Figure 16:
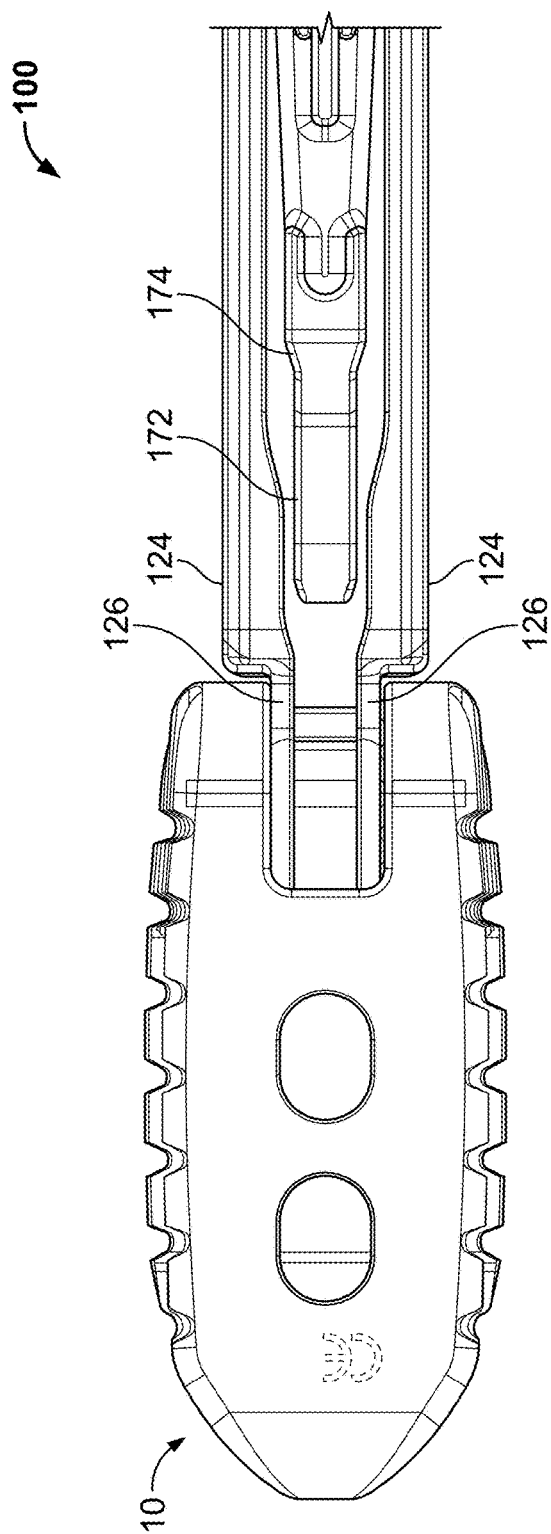
FIG. 16 is a plan view of the distal end of the insertion instrument of FIG. 12 inserted into the end of the spinal fusion implant of FIG. 1 in the unlocked configuration.

The insertion instrument 100 will now be described below with respect to each of its configurations. In the unlock position, pin 184 of the proximal gauge is positioned at the "unlock" position indicator 186 on the exterior of the elongate tubular element 106. As shown in FIGS. 15 A-B, spring 134 pushes on cam 136 which imparts a pushing force on internal ramp region 180 forcing lock button 138 into the inner bore 116 of the elongate tubular element 106. As depicted in FIG. 15 C, in the unlocked position, the inner shaft 108 is held its fully retracted position. Lateral wings 170 are positioned within the medial grooves 142 and lateral wing-receiving channels 152 and abutment prongs 176 push on ramps 150 to release the flexible arms such that the distal insertion members 126 are collapsed toward one another. In some implementations, the distal members 126 completely collapse towards one another, in other implementations, the distal insertion members 126 partially collapse towards one another. In this collapsed position, the insertion instrument 100 has the necessary clearance to insert the distal insertion members 126 into the spinal fusion implant 10 such that the rounded distal protrusion 154 is inserted into the pivot groove 36 of the engagement recess 34 (FIG. 16).

Figure 17A:
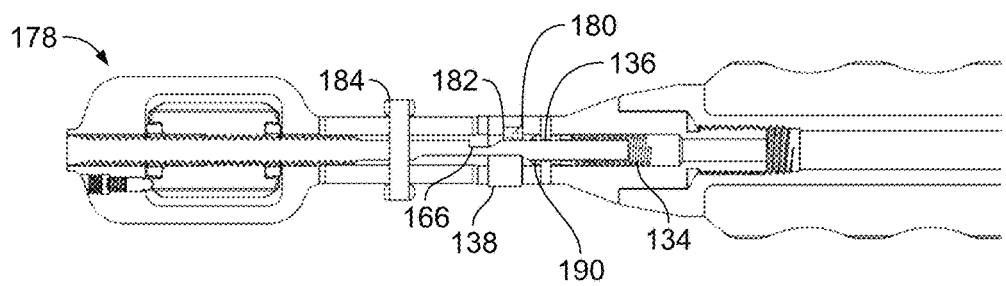
FIG. 17 A is a cross sectional view of the proximal end of the insertion instrument of FIG. 12 in a first transitional position as the insertion instrument is translated from the unlocked configuration to a locked configuration.
Figure 17B:
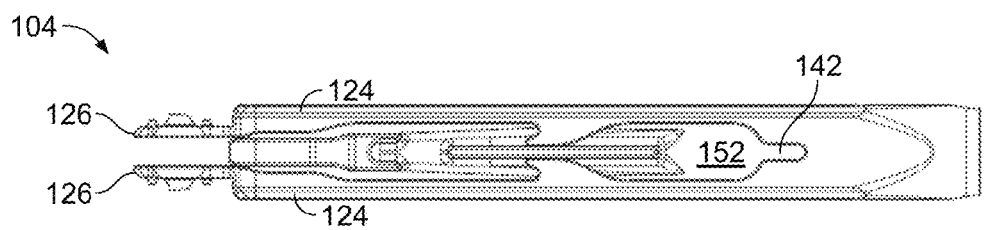
Figure 18A:
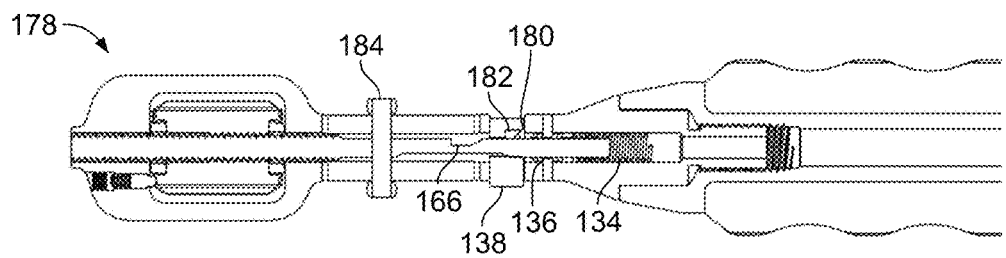
FIG. 18 A is a cross sectional view of the proximal end of the insertion instrument of FIG. 12 in a second transitional position as the insertion instrument is translated from the unlocked configuration to a locked configuration.
Figure 18B:
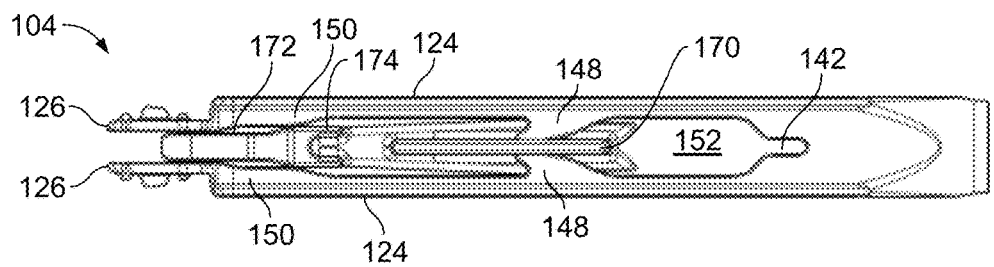

Spinning the thumbwheel 128 to the right moves the insertion instrument from the unlock configuration to the lock configuration. As the thumbwheel 128 spins, the proximal gauge 140 will begin to translate along the longitudinal slots 118 of the elongate tubular element 106 until it reaches the "lock" position indicator 186. FIGS. 17 A, 18 A, 19 A-B show cross sectional views of the actuation assembly 178 as the insertion instrument 100 translates to the locked configuration. Spring 134 imparts a pushing force on cam 136 which pushes on the internal ramp region 180 while ramp 190 on inner shaft 108 forces cam 136 from one side of the internal ramp region 180 to the other. Together these forces move the button 138 out of the elongate tubular element 106 via slot 120. When the insertion instrument 100 is locked, the inner shaft 108 resets button 138 from in to out so it will lock into cut-out 166 of inner shaft when instrument is later cycled from the lock to pivot configuration.

Figure 19A:
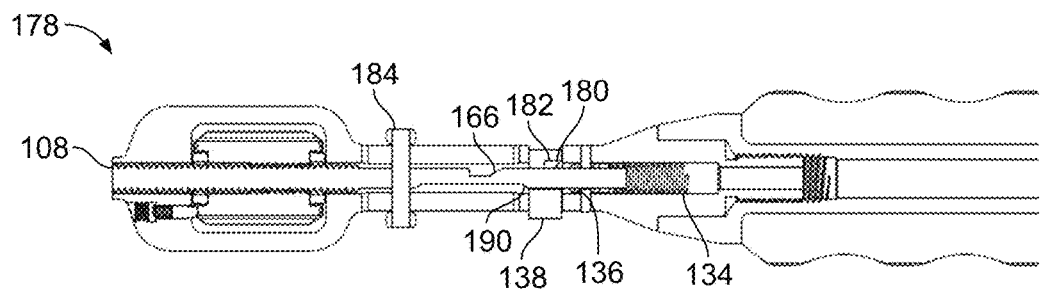
FIGS. 19 A-B are cross sectional views of the proximal end of the insertion instrument of FIG. 12 in a locked configuration.
Figure 19B:
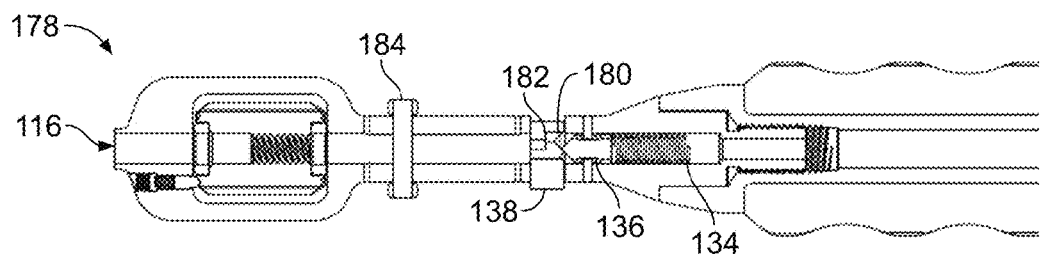
Figure 19C:
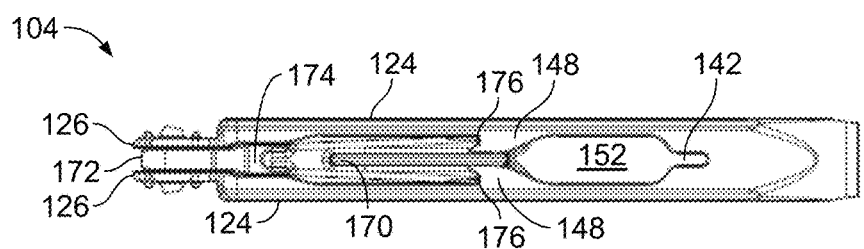

As the inner shaft 108 translates distally, the advancement head 172 begins to distract distal advancement ramps 150 and the distal insertion members 126. As depicted in FIG. 19 C, in the lock configuration, the inner shaft 108 is in its fully extended position such that the advancement head 172 is positioned between upper and lower distal insertion members 126 and support spacer 174 is positioned between upper and lower distal advancement ramps 150 which prevents the collapse of the flexible arms 124 and keeps the upper and lower distal insertion members 126 apart in a locked position. In this fully extended, maximal height position, the rounded distal portions 154 of the distal insertion members 126 engage in the engagement recess 34. In this position, the distance between distal insertion members 126 is sufficient to fully seat the large central protrusion 154 into the large central protrusion aperture 38 and each of the small radial protrusions 156 into their respective small radial protrusion aperture, thereby placing the insertion instrument 100 in a locked relationship with the spinal fusion implant 10.

Figure 20A:
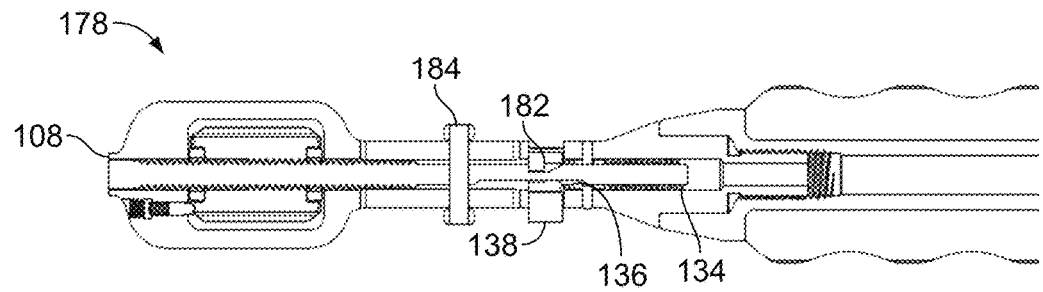
FIGS. 20 A-B are cross sectional views of the proximal end of the insertion instrument of FIG. 12 in a pivot configuration.
Figure 20B:
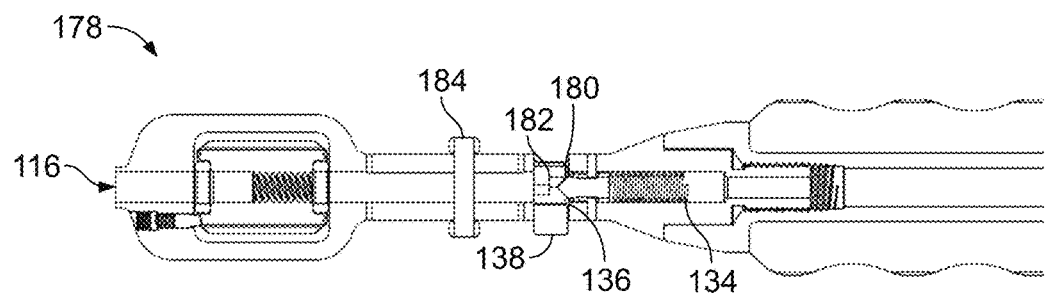
Figure 20C:
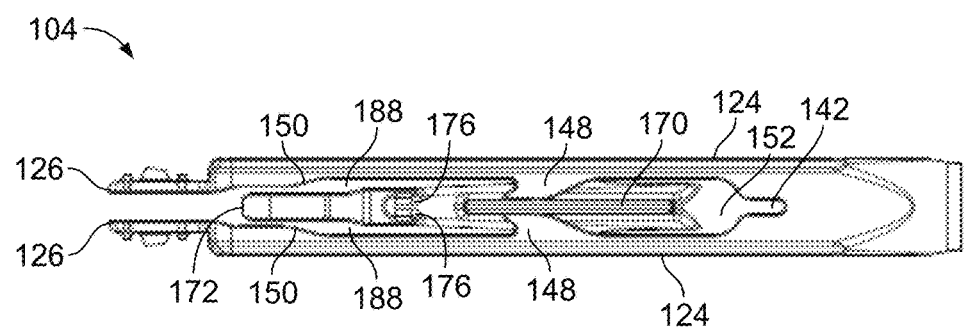
Figure 21:
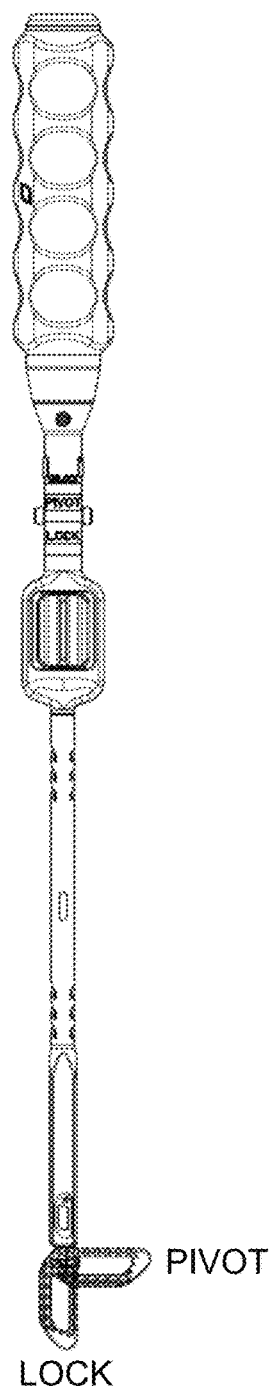
FIG. 21 is a plan view of the insertion instrument of FIG. 12 showing the spinal fusion implant of FIG. 1 in the locked and pivot configurations according to one embodiment.

Spinning the thumbwheel 128 to the left moves the insertion instrument from the locked configuration to the pivot configuration. As the thumbwheel 128 spins, the pin 184 on the proximal gauge 140 will being to translate within the longitudinal slot 118 until it reaches the "Pivot" position indicator 186 at which time there will be an indication that the instrument/implant is in the pivot configuration (e.g., a tactile stop, an audible click, etc.). FIGS. 20 A-C show the insertion instrument 100 in the pivot position. In the pivot position, pin 184 of the proximal gauge is positioned at the "Pivot" position indicator 186 on the exterior of the elongate tubular element 106. As shown in FIGS. 20 A-B, the spring 134 pushes on the cam 136, the cam 136 pushes on the internal ramp region 180 forcing the button 138 out. The button 138 falls into cut-out 166 on the inner shaft 108 thereby preventing the inner shaft 108 from retracting further.

As depicted in FIG. 20 C, in the pivot configuration the inner shaft 108 is partially retracted within the elongate tubular element 106. As the inner shaft 108 retracts, the advancement head 172 and support spacer 174 withdraw from the distal insertion members 126 and distal advancement ramps 150 until such location in which button 138/cut-out 166 interface (described above) prevents further retraction. Lateral wings 170 are positioned between proximal advancement ramps 148 and act as a spacer to keep the ramps 148 apart in the pivot position such that there are gaps 188 between the distal insertion head 168 and the flexible arms 124. These gaps 188 allow the flexible arms 124 to flex inward slightly such that the small radial protrusions 158 disengage from the small radial protrusion apertures 40. The spinal fusion implant 10 remains connected to the insertion instrument 100 via the engagement of large central protrusion 156 and large central protrusion aperture 38. The insertion instrument 100 may be maneuvered such that the spinal fusion implant 10 is free to pivot about its distal portion 104. The spinal fusion implant 10 pivots about the large central protrusion 156 until flat face 194 contacts pivot stop 48 and the implant has achieved the predetermined amount of rotation (by way of example, 60 or 90 degrees).

In order to switch between pivot and unlock configurations, the button 138 must be pressed in while positioned in pivot configuration. Recall that in the pivot configuration, the button 138 blocks the inner shaft 108 (FIGS. 20 A-B). Pressing the button 138 in clears the inner shaft 108 of the button 138 (FIGS. 16 A-B) to allow the thumbwheel 128 to be rotated to the left and the inner shaft 108 to be fully retracted. In the fully retracted position, the upper and lower flexible arms 124 are allowed to flex completely inward such that the large central protrusion 156 and small radial protrusions 158 retract from their respective apertures 38, 40 disengage from the spinal fusion implant 10 allowing the insertion instrument 100 to be removed.

According to another broad aspect of the present invention, the spinal fusion implant 10 is capable of being used in minimally invasive surgical procedures, needing only a relatively small operative corridor for insertion. By way of example only, the spinal fusion implant 10 will now be described in relation to a transforaminal lumbar interbody fusion (TLIF) technique, in which the intervertebral disc space is approached from a postero-lateral direction, however it should be understood that the spinal fusion implant 10 is capable of use in a variety of surgical procedures not described herein. After creation of this operative corridor and preparing the disc space (using techniques commonly known and used in the art), the spinal fusion implant 10 is mated to an insertion device 100 and advanced through the operative corridor toward the target intervertebral space.

First, the distal end 104 of the inserter 100 is inserted into the second lateral end 18 (trailing end) of the spinal fusion implant 10 via engagement recess 34. The insertion instrument 100 is locked to the spinal fusion implant 10 by spinning the thumbwheel 128 to the right until the proximal gauge 140 reaches the "lock" position. With the insertion instrument 100 in the lock configuration, the spinal fusion implant 100 may be impacted into the disc space.

Once the desired depth and position has been achieved, the insertion instrument 100 may be used to pivot the spinal fusion implant 10 by spinning the thumbwheel 128 to the left until the proximal gauge 140 reaches the "pivot" position. The user may receive an indication that the instrument/implant is in "pivot" position via, for example a tactile feedback, an audible click, etc. The spinal fusion implant 10 will remain connected to the insertion instrument 100 but is free to pivot about the distal portion 104 (e.g. by way of non-limiting example only, 60 or 90 degrees). Preferably, the spinal fusion implant 10 is impacted along the posterior margin of the annulus fibrosus until it reaches the anterior one-third of the intervertebral disc space.

In accordance with the present invention, the user is provided with one or more methods to aid in verifying desired positioning of the spinal fusion implant 10 using the external markers on at least one of the implant and the insertion instrument 100. According to a broad aspect, as the spinal fusion implant 10 rotates during pivoting, two or more markers (e.g., vertical stripes) move in relationship to one another from a given viewing perspective 202. The relative movement or position allows the user to identify the current rotational orientation of the spinal fusion implant 10.

According to a first embodiment, the marks may be positioned on one or more surfaces of the spinal fusion implant. FIG. 23 A shows the spinal fusion implant 10 within the disc space after it has been advanced along the operative corridor but before final alignment. FIG. 23 B is a trailing view of the second lateral end 18 (trailing end) of the spinal fusion implant. The engagement recess 34 is visible as are both markers 64. Marker 66 provided within the engagement recess 34 is not visible in this orientation. FIG. 23 C shows the spinal fusion implant 10 within the disc space after partial rotation but before final alignment. FIG. 23 D is a trailing view of the spinal fusion implant 10. Here, all of the markers 64, 66 may be visible but they are not yet in alignment. FIG. 23 E shows the spinal fusion implant 10 within the disc space after further rotation but before final alignment. FIG. 23 F is a trailing view of the spinal fusion implant 10. The markers 64 and 66 are closer together but not yet in the alignment. By looking at markers 64 and 66, the user may ascertain that the spinal fusion implant 10 is not properly aligned and more manipulation of the spinal fusion implant 10 must occur to achieve desired positioning. FIG. 23 G shows the spinal fusion implant 10 in the disc space after insertion is complete and the implant is placed in the desired alignment. FIG. 23 H shows a view of the posterior face 22 of the spinal fusion implant 10 after it has been rotated. Notably, vertical stripes 64, 66 are in axial alignment and appear to the user as an unbroken line.

Figure 24A:
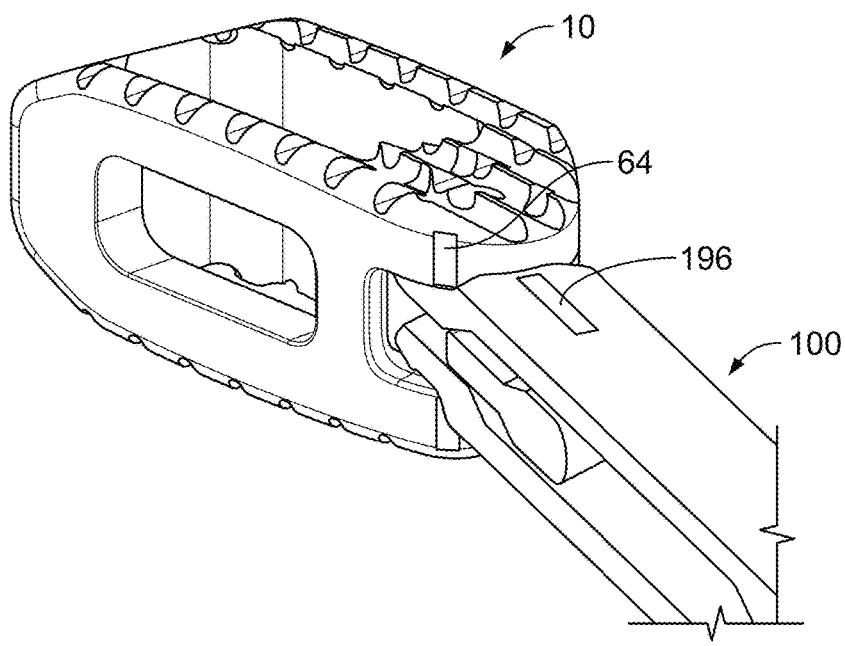
FIG. 24 A is a perspective view of the spinal fusion implant coupled to the insertion instrument in a first alignment position as indicated by external alignment makers on the implant and instrument.
Figure 24B:
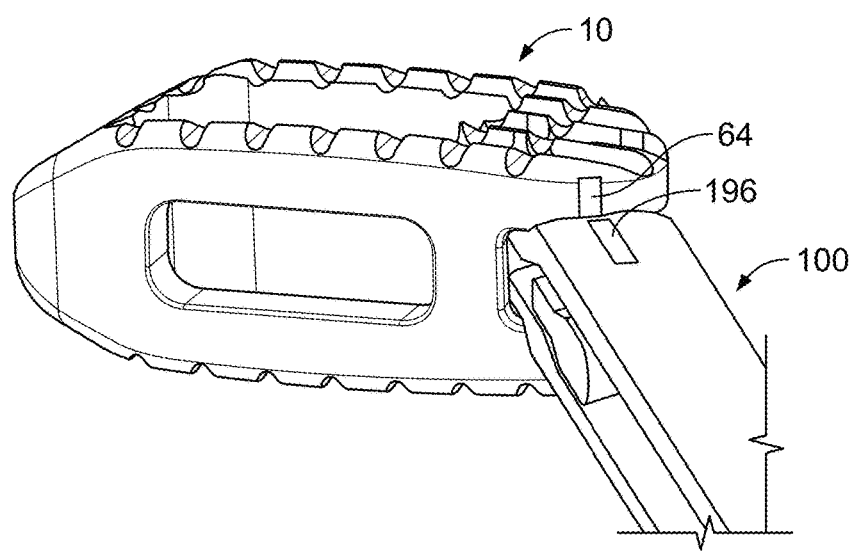

According to a second embodiment, the marks may be positioned on one or more surfaces of the spinal fusion implant and one or more surfaces of the insertion instrument. As shown in FIGS. 24 A-B, because the marks 64, 196 are separated and are on the insertion instrument and spinal fusion implant, the relative position can be used to identify the current rotation of the spinal fusion implant 10 in relation to the insertion instrument. The markers 64, 196 may be placed in such a way that they create a specific orientation when the spinal fusion implant 10 is in a desired position. By way of example, the markers 64, 196 can align and create a straight line when the spinal fusion implant 10 is in the desired final position. As the spinal fusion implant 10 is pivoted relative to the insertion instrument 100 within the intervertebral disc space, the markers 64 will align with the marker 196 on the inserter. When the visual indicator markers are in alignment (FIG. 24 B), the user will know that the spinal fusion implant 10 has achieved desired rotational orientation within the intervertebral disc space.

In accordance with the present invention, the user is provided with one or more methods to aid in verifying the desired positioning of the spinal fusion implant 10 using lateral and/or anterior/posterior (A/P) fluoroscopy to localize internal visualization markers and verify movement of the spinal fusion implant 10 within the disc space.

Figure 9:
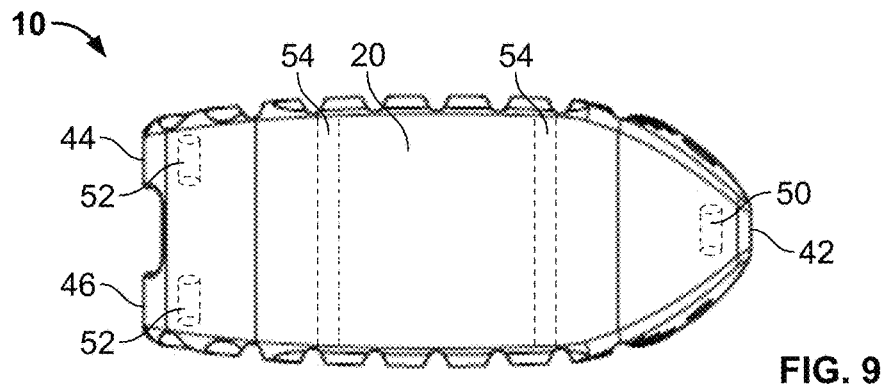
FIG. 9 is a plan view of the spinal fusion implant of FIG. 1 showing internal radiographic markers according to one embodiment.
Figure 25B:
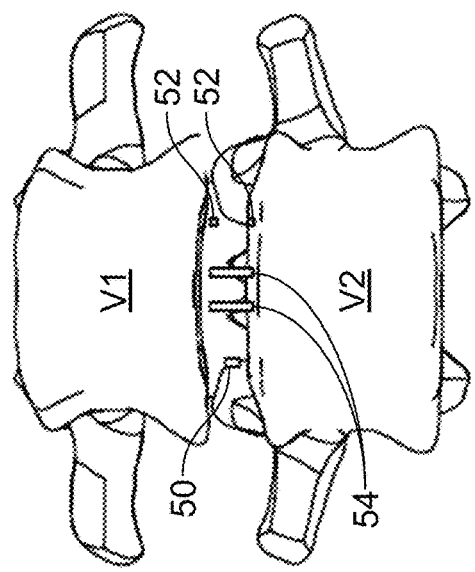
FIGS. 25 A-B are examples of lateral and anterior-posterior x-rays indicating the final positioning of the spinal fusion implant via internal visualization markers of the implant according to the embodiment of FIG. 9.
Figure 25A:
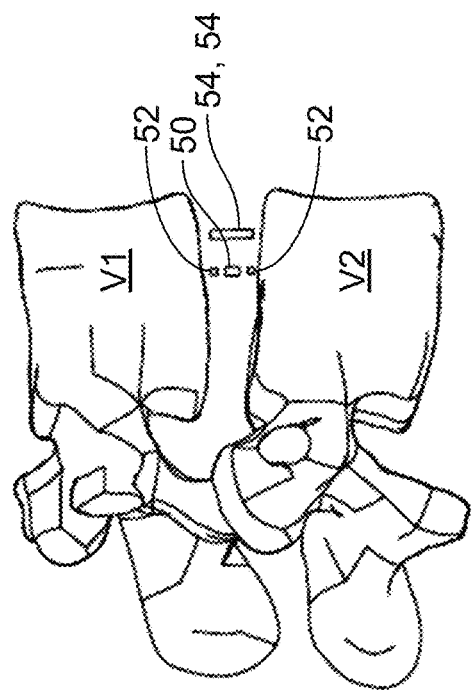

According to a first embodiment, there is provided a confirmation method using fluoroscopy to localize internal visualization markers to verify movement of the spinal fusion implant 10 of FIG. 9 within the disc space. As the spinal fusion implant 10 is impacted into the disc space via insertion instrument 100 but before pivoting, radiographic markers 54 will appear side-by-side on lateral fluoroscopy. As the spinal fusion implant 10 is pivoted, markers 54 appear to move closer to one another and align with one another when spinal fusion implant 100 is rotated into the desired rotational orientation. Markers 50, 52 will also align with one another in this rotational orientation. FIG. 25 A is an example lateral x-ray depicting what radiographic markers 50, 52, 54 would look like with spinal fusion implant 10 in this orientation. On anterior-posterior fluoroscopy, the spinous process will be positioned in between radiographic markers 54 when the spinal fusion implant 100 is placed in the desired orientation. Markers 50, 52 may be used to determine the final location of the implant between lateral aspects of the intervertebral space. FIG. 25 B is an example anterior-posterior x-ray depicting what radiographic markers 50, 52, 54 would look like with spinal fusion implant 10 in the desired orientation.

Figure 26A:
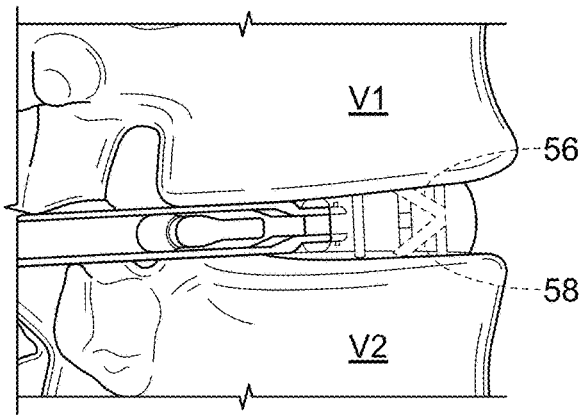
FIGS. 26 A-C are examples of lateral x-rays indicating first, second, and third transitional positions of the spinal implant as indicated via directional internal visualization makers according to the embodiment of FIG. 10.
Figure 26B:
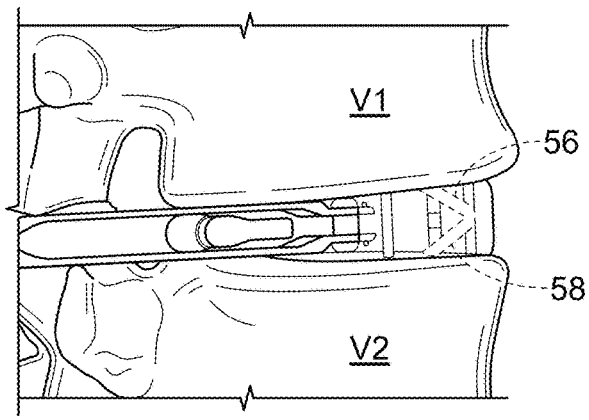
Figure 26C:
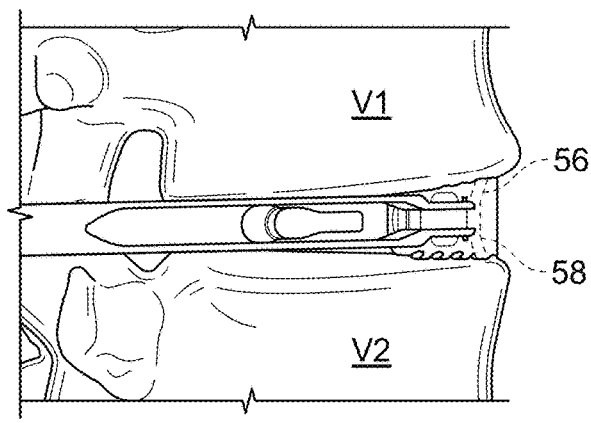
Figure 27B:
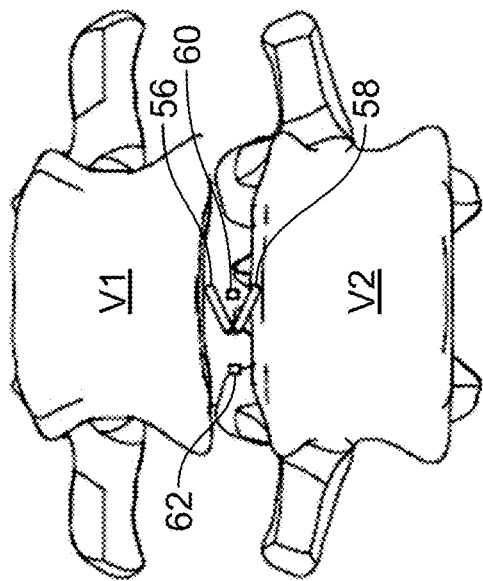
FIGS. 27 A-B are examples of lateral and anterior-posterior x-rays indicating the final positioning of the spinal fusion implant via visualization markers according to the embodiment of FIG. 10.
Figure 27A:
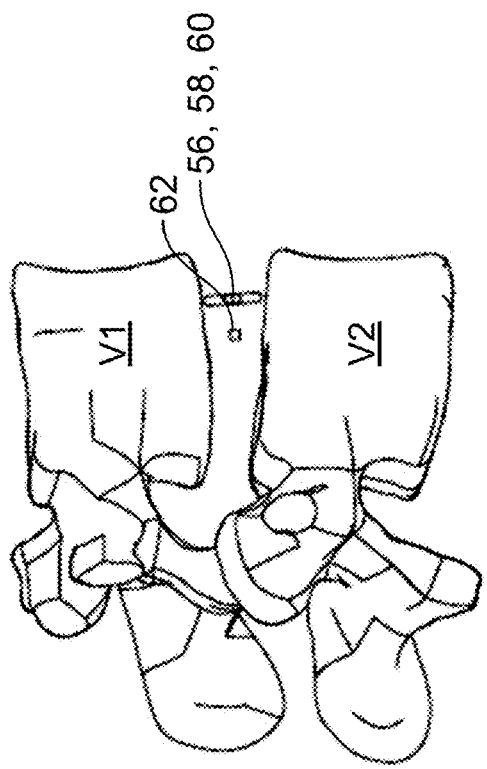

According to a second embodiment, there is provided a confirmation method using the internal visualization markers described above with respect to FIG. 10. Using lateral fluoroscopy, as the spinal fusion implant 10 is impacted into the disc space via insertion instrument 100 but before pivoting, the radiographic markers 56, 58 converge to form an arrow that points towards the anterior aspect of the intervertebral disc space during impaction (FIG. 26 A). As the spinal fusion implant 10 is pivoted, the arrow gets thicker as it pivots, pointing less and less (FIG. 26 B), until the two lines converge (along with midline radiographic marker 60) into what appears to be a single line. If the spinal fusion implant 10 is over rotated, the angled markers 56, 58 begin to point towards the posterior aspect of the intervertebral disc space (FIG. 26C). In this way, the directional arrows inform the user which direction to rotate the spinal fusion implant 10 to get it back into rotational alignment. FIG. 27 A is an example lateral x-ray depicting what radiographic markers would look like with spinal fusion implant 10 in the desired rotational orientation with radiographic markers 56, 58, 60 aligning into one single line. Using anterior-posterior fluoroscopy, the spinal fusion implant 10 is positioned within the desired position when radiographic marker 60 is aligned with the spinous process. Markers 60 may be used to determine the final location of the implant between lateral aspects of the intervertebral space. FIG. 27 B is an example anterior-posterior x-ray depicting what radiographic markers 54, 56, 58, 60 would look like with spinal fusion implant 10 in the desired orientation.

Following final positioning, the insertion instrument 100 may be removed from the spinal fusion implant 100 by pressing the button 138 inwards towards inner bore 116 and spinning the thumbwheel 128 to the left until the proximal gauge 140 reaches the "unlock" position. The distal insertion members 126 will then collapse and the insertion instrument 100 may be disengaged from the spinal fusion implant 100.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant for insertion between first and second vertebral bodies, each vertebral body having a cancellous bone interior bounded by a cortical bone exterior wall, each vertebral body having a curved anterior portion and a posterior portion curved to a lesser extent than the anterior portion, said posterior portion adjacent to a spinal canal, said spinal fusion implant comprising:

a first vertebral body engagement side and a second vertebral body engagement side opposing said first vertebral body engagement side, an anterior side and a posterior side opposing said anterior side, a first end portion and a second end portion, a longitudinal axis extending through said first end portion and said second end portion, a central aperture situated between the first end portion and the second end portion and extending through the first vertebral body engagement side and the second vertebral body engagement side, a transverse plane extending from the anterior side to the posterior side at a right angle to the longitudinal axis and passing through a proximal-most point of the central aperture, said second end portion further including an engagement recess that extends distally toward the central aperture from a proximal end of the implant to a position short of the transverse plane and separates the second end portion into a top portion and a bottom portion, the top portion having at least one top aperture extending therethrough and configured to temporarily receive a complementary engagement feature on an insertion tool, and the bottom portion having at least one bottom aperture extending therethrough and configured to temporarily receive a complementary engagement feature on an insertion tool, wherein said top portion includes a top exterior surface forming part of the first vertebral body engagement side and a top interior surface, said bottom portion includes a bottom exterior surface forming part of the second vertebral body engagement side and a bottom interior surface, the at least one top aperture opening through said top exterior surf ace and said top interior surface, and the at least one bottom aperture opening through said bottom exterior surface and said bottom interior surface, wherein said at least one top aperture comprises a top center aperture and a plurality of smaller top radial apertures arranged around the top center aperture and said at least one bottom aperture comprises a bottom center aperture and a plurality of smaller bottom radial apertures arranged around the bottom center aperture.

2. The implant of claim 1, further comprising a first radiographic marker embedded at least partially within said anterior side.

3. The implant of claim 1, wherein said first vertebral body engagement side and said second vertebral body engagement side are each at least one of generally planar, generally convex, and generally concave.

4. The implant of claim 1, wherein said anterior side is generally convexly curved.

5. The implant of claim 1, further comprising at least one posterior aperture extending from the posterior side of the implant into the central aperture.

6. The implant of claim 1, wherein said implant is made of at least one of polyether-ether-ketone, poly-ether-ketone-ketone, ceramic, metal, and any combination of poly-ether-ether-ketone, poly-ether-ketone-ketone, ceramic, and metal.

7. The implant of claim 1, wherein at least one of said first vertebral body engagement side and said second vertebral body engagement side is provided with an anti-migration feature.

8. The implant of claim 7, wherein said anti-migration feature comprises a plurality of ridges.

9. The implant of claim 1, wherein said first end portion is adapted to be inserted into an intervertebral space through a postero-lateral approach and rotated to extend to a contralateral side of the intervertebral space.

10. A spinal fusion implant for insertion between first and second vertebral bodies, each vertebral body having a cancellous bone interior bounded by a cortical bone exterior wall, each vertebral body having a curved anterior portion and a posterior portion curved to a lesser extent than the anterior portion, said posterior portion adjacent to a spinal canal, said spinal fusion implant comprising:

a first vertebral body engagement side and a second vertebral body engagement side opposing said first vertebral body engagement side, an anterior side and a posterior side opposing said anterior side, a first end portion and a second end portion, a longitudinal axis extending through said first end portion and said second end portion, a central aperture situated between the first end portion and the second end portion and extending through the first vertebral body engagement side and the second vertebral body engagement side, a transverse plane defined as extending through the implant from the anterior side to the posterior side at a right angle to the longitudinal axis and passing through a proximal-most point of the central aperture, said second end portion further including an engagement recess that extends distally toward the central aperture from a proximal end of the implant to a position short of the transverse plane and separates the second end portion into a top portion and a bottom portion, the top portion having at least one top aperture extending therethrough and configured to temporarily receive a complementary engagement feature on an insertion tool, and the bottom portion having at least one bottom aperture extending therethrough and configured to temporarily receive a complementary engagement feature on an insertion tool;

further comprising a first radiographic marker embedded at least partially within said anterior side; and further comprising a second radiographic marker embedded at least partially within said anterior side below the first radiographic marker, the first and second radiographic markers situated in a converging relationship such that ends of the first and second radiographic markers oriented towards the implant first end portion are closer to each other than ends of the first and second radiographic markers oriented towards the implant second end portion.

11. The implant of claim 10, wherein said first vertebral body engagement side and said second vertebral body engagement side are each at least one of generally planar, generally convex, and generally concave.

12. The implant of claim 10, wherein said anterior side is generally convexly curved.

13. The implant of claim 10, further comprising at least one posterior aperture extending from the posterior side of the implant into the central aperture.

14. The implant of claim 10, wherein said implant is made of at least one of polyether-ether-ketone, poly-ether-ketone-ketone, ceramic, metal, and any combination of poly-ether-ether-ketone, poly-ether-ketone-ketone, ceramic, and metal.

15. The implant of claim 10, wherein at least one of said first vertebral body engagement side and said second vertebral body engagement side is provided with an anti-migration feature.

16. The implant of claim 15, wherein said anti-migration feature comprises a plurality of ridges.

17. The implant of claim 10, wherein said first end portion is adapted to be inserted into an intervertebral space through a postero-lateral approach and rotated to extend to a contralateral side of the intervertebral space.

* * * * *